(12) United States Patent
Liou

(10) Patent No.: US 11,770,888 B2
(45) Date of Patent: Sep. 26, 2023

(54) AMBIENT LIGHTING FOR IMPROVING SLEEPING DISORDERS, COGNITION AND/OR NEUROLOGICAL DISORDERS

(71) Applicant: NATIONAL YANG MING CHIAO TUNG UNIVERSITY, Hsinchu (TW)

(72) Inventor: Yiing-Mei Liou, Taipei (TW)

(73) Assignee: NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 17/704,671

(22) Filed: Mar. 25, 2022

(65) Prior Publication Data

US 2022/0312571 A1    Sep. 29, 2022

Related U.S. Application Data

(60) Provisional application No. 63/165,917, filed on Mar. 25, 2021.

(51) Int. Cl.
*H05B 47/11* (2020.01)
*H05B 47/175* (2020.01)
(Continued)

(52) U.S. Cl.
CPC .......... *H05B 47/11* (2020.01); *A61N 5/0618* (2013.01); *H05B 45/10* (2020.01); *H05B 45/20* (2020.01);
(Continued)

(58) Field of Classification Search
CPC .......... A61N 5/0618; A61N 2005/0626; A61N 2005/0636; A61N 2005/0652;
(Continued)

(56) References Cited

U.S. PATENT DOCUMENTS

| 8,852,254 B2 | 10/2014 | Moscovici |
| 8,858,607 B1 | 10/2014 | Jones |

(Continued)

FOREIGN PATENT DOCUMENTS

| CN | 101563648 A | 10/2009 |
| JP | 5808318 B2 | 11/2015 |

(Continued)

OTHER PUBLICATIONS

The partial European search report issued in European Application No. 22164261.4, dated Aug. 22, 2022.
(Continued)

*Primary Examiner* — Raymond R Chai
(74) *Attorney, Agent, or Firm* — HAMRE, SCHUMANN, MUELLER & LARSON, P.C.

(57) ABSTRACT

Alight system used in an ambient environment is provided. The light system comprises an emitting device and a controller coupled to the emitting device. The emitting device is configured to provide a light impinging on a subject in the ambient environment. The controller is configured to control the emitting device. The light provided by the emitting device has at least 30% green light. A line extending from the emitting device to the subject and a plane at eye level of the subject in the ambient environment forms an angle of about 45 degrees. The light has a horizontal illuminance of about 2200 lux to about 2800 lux.

18 Claims, 27 Drawing Sheets

(51) Int. Cl.
*H05B 47/115* (2020.01)
*H05B 45/20* (2020.01)
*H05B 45/10* (2020.01)
*A61N 5/06* (2006.01)

(52) U.S. Cl.
CPC ......... *H05B 47/115* (2020.01); *H05B 47/175* (2020.01); *A61N 2005/0626* (2013.01); *A61N 2005/0652* (2013.01)

(58) Field of Classification Search
CPC ............ A61N 2005/0662; H05B 45/10; H05B 45/20; H05B 47/11; H05B 47/115; H05B 47/175; Y02B 20/40
See application file for complete search history.

(56) References Cited

U.S. PATENT DOCUMENTS

| | | | |
|---|---|---|---|
| 9,802,060 B2 | 10/2017 | Olds et al. | |
| 10,786,648 B2* | 9/2020 | Berman | A61M 21/00 |
| 11,071,177 B2* | 7/2021 | Gordin | A61N 5/0618 |
| 11,184,967 B2* | 11/2021 | Coleman | H05B 47/11 |
| 11,497,721 B2* | 11/2022 | Tabuteau | A61P 25/34 |
| 11,503,270 B1* | 11/2022 | Timonen | G06T 19/006 |
| 2005/0073839 A1 | 4/2005 | Pederson et al. | |
| 2012/0206050 A1* | 8/2012 | Spero | B60Q 1/1423 |
| | | | 315/152 |
| 2012/0253427 A1 | 10/2012 | Aunio et al. | |
| 2014/0277294 A1 | 9/2014 | Jones et al. | |
| 2014/0288351 A1 | 9/2014 | Jones | |
| 2015/0061506 A1* | 3/2015 | Baaijens | H05B 47/11 |
| | | | 315/152 |
| 2015/0062892 A1 | 3/2015 | Krames et al. | |
| 2015/0289347 A1* | 10/2015 | Baaijens | A61N 5/0618 |
| | | | 315/294 |
| 2016/0016005 A1 | 1/2016 | Olds et al. | |
| 2017/0367785 A1* | 12/2017 | Munari | H05B 47/19 |
| 2019/0160252 A1* | 5/2019 | Krames | F21K 9/232 |
| 2019/0350066 A1* | 11/2019 | Herf | H05B 47/105 |
| 2020/0178892 A1* | 6/2020 | Maslik | A61B 5/4836 |
| 2020/0205261 A1* | 6/2020 | Skov Hansen | F21S 10/02 |
| 2020/0332969 A1* | 10/2020 | Soler | F21K 9/66 |
| 2021/0176841 A1* | 6/2021 | Borra | H05B 47/17 |
| 2022/0110194 A1* | 4/2022 | Vissenberg | H05B 45/10 |

FOREIGN PATENT DOCUMENTS

| | | | |
|---|---|---|---|
| KR | 1020170024983 A | 3/2017 | |
| WO | 2006087723 A2 | 8/2006 | |
| WO | 2018152255 A1 | 8/2018 | |
| WO | WO-2019068665 A1 * | 4/2019 | ............ H05B 31/50 |

OTHER PUBLICATIONS

Liu et al., "Ambient bright lighting in the morning improves sleep disturbances of older adults with dementia", Elsevier, Sleep Med, Published Oct. 21, 2021, 9 pages provided.

Liu et al., "Pilot Study of the Effects of Bright Ambient Therapy on Dementia Symptoms and Cognitive Function", Frontiers in Psychology, Published Dec. 24, 2021, 13 pages provided.

* cited by examiner

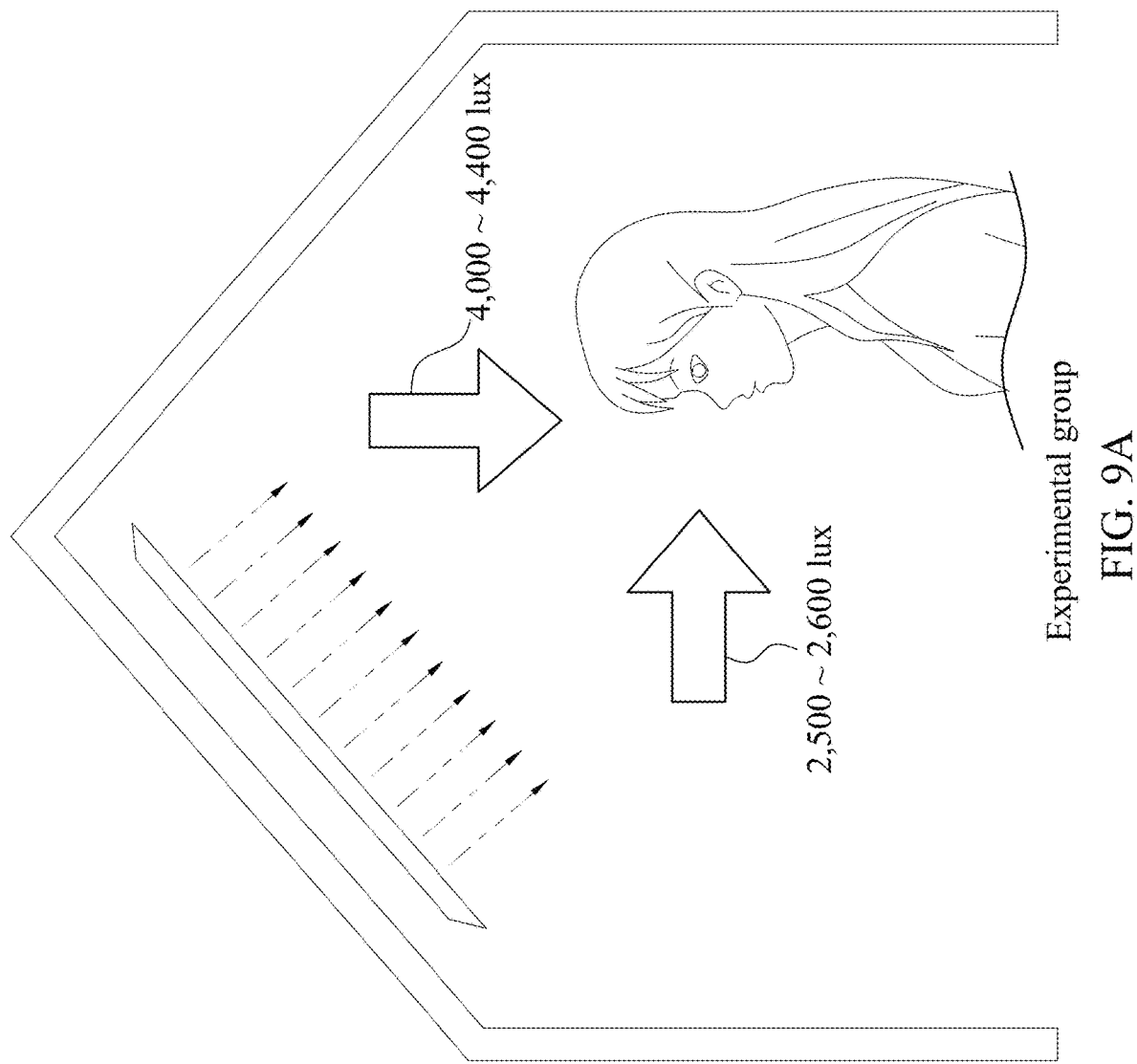

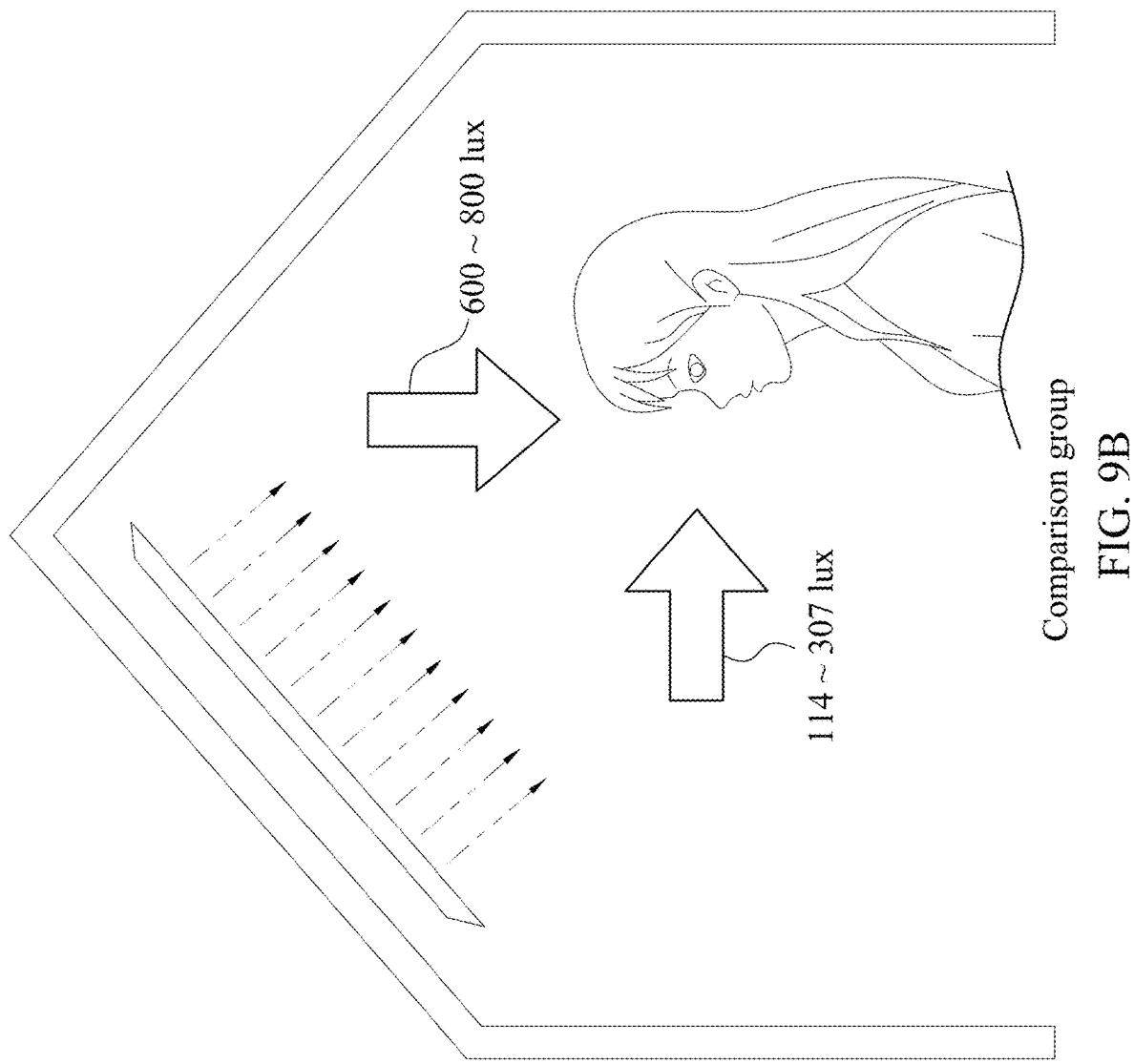

PS: * $P < 0.05$, ** $P < 0.01$

Higher score reflects a more severe level of neuropsychiatric behaviors

PS: * $P < 0.05$, ** $P < 0.01$
Higher score reflects a more severe level of neuropsychiatric behaviors

PS: * $P < 0.05$, ** $P < 0.01$

Higher score reflects a more severe level of neuropsychiatric behaviors

AMBIENT LIGHTING FOR IMPROVING SLEEPING DISORDERS, COGNITION AND/OR NEUROLOGICAL DISORDERS

BACKGROUND

1. Field of the Disclosure

The present disclosure provides a system and method of providing ambient lighting for improving sleeping quality, circadian rhythms, cognitive function, neurological disorder, depression, emotional status, heart rate variability, sympathetic activity and/or parasympathetic activity.

2. Description of Related Art

Light therapy is a way to treat seasonal affective disorder (SAD) and certain other conditions by exposure to artificial light. Light therapy is thought to affect brain chemicals linked to mood and sleep while easing SAD symptoms. Using a light therapy box may also help with other types of depression, sleep disorders and other conditions. Light therapy is also known as bright light therapy or phototherapy. Several studies have shown that light intensity and the color/hue of light impacts human health, and various health-related technologies based on illumination have been proposed.

The current phototherapy cannot achieve satisfied improvement in sleep efficiency, affective disorder and other psychological disorders. Phototherapy technology continues to seek improved phototherapy methods and devices providing desirable illumination characteristics capable of overcoming the challenges associated with conventional phototherapy methods and devices.

SUMMARY

According to one example embodiment of the instant disclosure, a light system used in an ambient environment comprises an emitting device and a controller coupled to the emitting device. The emitting device is configured to provide a light impinging on a subject in the ambient environment. The controller is configured to control the emitting device. The light provided by the emitting device has at least 30% green. A line extending from the emitting device to the subject and a plane at eye level of the subject in the ambient environment forms an angle of about 45 degrees. The light has a horizontal illuminance of about 2200 lux to about 2800 lux.

According to another example embodiment of the instant disclosure, a light system in an ambient environment comprises an emitting device and a controller connected to the emitting device. The emitting device is configured to provide a light into the ambient environment, wherein the light has at least 30% green light spectral component. The controller comprises a control module configured to control the emitting device, a sensing module configured to detect an illuminance value of the light provided by the emitting device; and a control interface in communication with the control module.

According to another example embodiment of the instant disclosure, a method for providing ambient lighting for improving sleeping quality in a subject comprises: providing a light into an ambient environment, wherein a ratio of a blue-green light spectral component with a wavelength from around 450 nm-580 nm is increased to at least 30%; and exposing the subject to the light.

In order to further understanding of the instant disclosure, the following embodiments are provided along with illustrations to facilitate appreciation of the instant disclosure; however, the appended drawings are merely provided for reference and illustration, and do not limit the scope of the instant disclosure.

BRIEF DESCRIPTION OF THE DRAWINGS

FIG. 9A and FIG. 9B show illumination models of the experimental and comparison groups.

DETAILED DESCRIPTION

Figure 1:
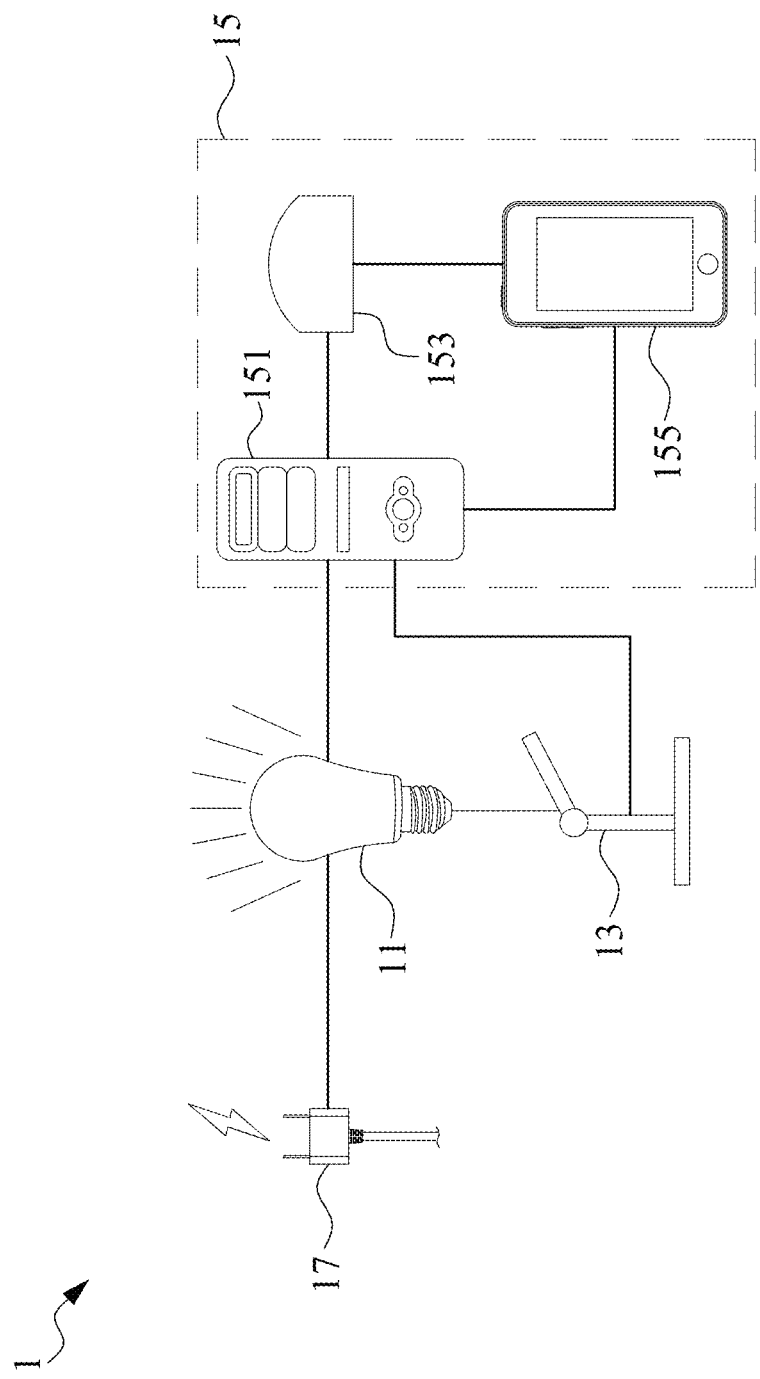
FIG. 1 is a block diagram schematically illustrating the configuration of a light system in accordance with an embodiment of the instant disclosure.

In the following detailed description, for purposes of explanation and not limitation, example embodiments disclosing specific details are set forth to provide a thorough understanding of various principles and aspects. However, it will be apparent to one having ordinary skill in the art, having had the benefit of the present disclosure, that the claimed subject matter may be practiced in other embodiments that depart from the specific details disclosed herein. Moreover, descriptions of well-known devices, methods and materials may be omitted so as not to obscure the description of various principles set forth herein. Finally, wherever applicable, like reference numerals refer to like elements.

Terms not specifically defined herein should be understood according to the meanings that would be given to them by one of skill in the art in light of the disclosure and the context. As used in the specification, however, unless specified to the contrary, the following terms have the meaning indicated according to the following conventions.

The terms "disease" and "disorder" herein can be used interchangeably.

The terms "subject," "individual," and "patient" may be used interchangeably herein and typically refer to a mammal, in certain embodiments a human or a non-human primate.

The term "lux" refers to a unit of light measurement that takes area into account, representing light intensity. Lux is effective for measuring the amount of light output in a given area, where one lux is equal to one lumen per square meter. Lux is a great measurement for determining what we see as the brightness of a beam. Lux also determines the magnitude of light intensity travelling over distances.

The terms "light source" and "illumination source" are used interchangeably and refer to a device that provides light typically within the visible spectrum for humans.

When humans are exposed to light, the body is signaled to release the hormone cortisol, which is necessary for fighting stress. It also alerts the brain, thereby determining your mood. Lack of light can affect circadian rhythm, which is the body's 24-hour sleep/wake cycle. Sun exposure stimulates the hypothalamus in the brain which helps animals control their circadian rhythm. When the circadian rhythm is dysregulated, the brain may produce too much melatonin and less serotonin. Therefore, in short, lack of light causes humans to feel tired and unhappy.

Light therapy has long been a recognized treatment option for depression and insomnia, etc. Although light therapy has been recognized to be efficacious to treat a wide variety of indications, light therapy nonetheless remains underutilized as a therapy. For light therapy to be properly applied to a patient in need of treatment, several variables must be selected and repeatedly monitored throughout the course of the treatment. These parameters include wavelength, energy density, power density and timing of the applied light, as well as any associated patient-specific parameters. A less than optimal choice of parameters can result in reduced effectiveness of the treatment, or even adverse therapeutic outcomes.

The present disclosure surprisingly found that ambient lighting provided by at least 30% or 30% green light or green spectral component of a light can improve sleeping disorders, cognition and/or neurological disorders and at the same time will not affect vision. Accordingly, a light system and method was developed to provide the ambient lighting.

FIG. 1 is a block diagram schematically illustrating the configuration of a light system 1 in accordance with an embodiment of the instant disclosure. As shown in FIG. 1, the light system may include emitting device 11, an adjusting mechanism 13 connected to the emitting device 1, a controller 15 coupled to the emitting device 11 and the adjusting mechanism 13 and a power portion 17 electrically connected to the emitting device 1.

The emitting device 11 may include at least one light sources. The light sources are objects that provide light, increasing visibility. The emitting device 11 comes in many different varieties and supply differing quantities and qualities of light. The emitting device 11 may provide a light source providing at least 20% (preferably at least 30%) green light or green spectral component of a light. Ratio of the green light can be calculated by defining the areas of the spectrum of the green regions relative to the entire spectrums. In some embodiments of the present disclosure, the emitting device includes a tungsten lamp, a halogen lamp, a xenon arc lamp, a CP lamp or a light-emitting diode (LED). In some embodiments of the present disclosure, the emitting device 11 comprise at least 20%, 30%, 40%, 50%, or 60% green light or green spectral component of a light. Preferably, the emitting device 11 may comprise about 20% to about 60%, about 30% to about 60% or about 30% to about 50% green light or green spectral component of a light.

In some embodiments of the present disclosure, the emitting device 11 includes multiple wavelengths of the green light or a green spectral component of a light. Examples of the wavelength include, but are not limited to, from about 480 nm up to about 580 nm, or from about 500 nm up to about 535 nm, or from about 500 nm up to about 530 nm, or from about 510 nm up to about 550 nm, or from about 510 nm up to about 540 nm, or from about 510 nm up to about 530 nm, or from about 520 nm up to about 550 nm, or from about 520 nm up to about 540 nm, or from about 530 nm up to about 580 nm. In some embodiments of the present disclosure, the wavelength of the green light or the green spectral component of a light ranges from about 480 nm to 580 nm. In some embodiments of the present disclosure, the emitting device includes a blue-green light with a wavelength from about 450 nm to 580 nm.

In addition to the green light, the emitting device may provide several parameters, alone or in combination, to achieve advantageous improvements in light therapy.

As stated above, the emitting device 11 may provide at least 20% (preferably 430%) green light or green spectral component of a light. In some embodiments of the present disclosure, the emitting device provides at least 30% green light or green spectral component of a light and the green light spectral component or the green spectral component (or the blue-green light spectral component or the blue-green spectral component) has a wavelength from about 450 nm to about 580 nm. In some embodiments of the present disclosure, the green light spectral component or the green spectral component has a wavelength from about 480 nm to about 580 nm. In some embodiments of the present disclosure, such ratio of the green light or green spectral component of a light may be achieved by increasing the green light or the green spectral component of the light provided by the emitting device 11. In some embodiments of the present disclosure, such ratio of the green light or green spectral component of a light may be achieved by decreasing the blue light or the blue spectral component of the light provided by the emitting device 11. In some embodiments of the present disclosure, a ratio of the blue light or a blue light spectral component with a wavelength from around 415 nm-460 nm is decreased and a ratio of the blue light or a blue light spectral component with a wavelength from around 465 nm-490 nm is maintained. In some embodiments of the present disclosure, the light spectrum of the light provided by the emitting device 11 is the same as, or similar to, the solar spectrum.

Further, a color fidelity (Rf) of the light provided by the emitting device 11/a gamut (Rg) of the light provided by the emitting device may be greater than 90/95.

Illuminance is the measure of how much light illuminates a surface. Illuminance is the amount of light falling on a vertical surface or plane. Illuminance is measured in the unit "lux" and on a vertically positioned hypothetical surface. In addition, verticality can have different directions, including vertical to camera and to audience. The emitting device 11 may provide light having a total illuminance and/or a illuminance of the green light or the green spectral component of at least about 2,000 lux about 2200 lux, about 2,500 lux, about 2800 lux, about 3,000 lux, about 3600 lux, about 4,000 lux, about 4400 lux or about 4800 lux. Preferably, the illuminance and/or a illuminance of the green light or the green spectral component is measured at the ear, eye, or top-of-the-head height level of the subject. In some embodiments of the present disclosure, the illuminance includes a vertical illuminance which is the amount of light falling on a horizontal surface or plane at the ear, eye, or top-of-the-head height level of the subject and a horizontal illuminance which is the amount of light falling on a vertical surface or plane at the ear, eye, or top-of-the-head height level of the subject. In some embodiments of the present disclosure, the emitting device 11 may provide light having a total vertical illuminance and/or a vertical illuminance of the green light or the green spectral component of at least about 2,000 lux, about 2,500 lux, about 3,000 lux, about 3600 lux, about 4,000 lux, about 4,400 lux or about 4,800 lux. In some embodiments of the present disclosure, the emitting device 11 may provide light having a total horizontal illuminance and/or a horizontal illuminance of the green light or the green spectral component of at least 15 lux, about 300 lux, about 350 lux, about 400 lux, about 500 lux, about 750 lux, about 1000 lux, about 1500 lux, about 2000 lux, about 2200 lux, about 2500 lux or about 2800 lux.

A color rendering index (CRI) is a quantitative measure of the ability of a light source to reveal the colors of various objects faithfully in comparison with an ideal or natural light source. In some embodiments of the present disclosure, the color rendering index (%) of the emitting device 11 is higher than about 70, about 75, about 80, about 85, about 90 or about 95. In some embodiments of the present disclosure, the CRI of the emitting device 11 ranges from about 70 to about 98, about 70 to about 95, about 70 to about 90, about 70 to about 85, about 70 to about 80, about 75 to about 98, about 75 to about 95, about 75 to about 90, about 75 to about 85, about 80 to about 98, about 80 to about 95, about 80 to about 90, about 80 to about 85, about 85 to about 98, about 85 to about 95, about 85 to about 90 or about 90 to about 98.

Color quality scale (CQS) is a color rendering index (a quantitative measure of the ability of a light source to reproduce colors of illuminated objects). In some embodiments of the present disclosure, the CQS of the emitting device 11 ranges from about 20 to about 90, about 65 to about 95, about 65 to about 90, about 65 to about 85, about 65 to about 80, about 65 to about 75, about 70 to about 98, about 70 to about 95, about 70 to about 90, about 70 to about 85, about 70 to about 80, about 75 to about 98, about 75 to about 90, about 75 to about 85, about 80 to about 98, about 80 to about 90, about 85 to about 98 or about 85 to about 95.

Color temperature is a way to describe the light appearance provided by a light source. It is measured in degrees of Kelvin (K) on a scale from 1,000 to 10,000. In some embodiments of the present disclosure, the emitting device 11 provides at least 1,850 K, at least 2,500 K, at least 2,800 K, at least 3,000 K, at least 3,500 K, at least 5,000 K, at least 5,500 K, at least 6,500 K, at least 8,000 K or at least 10,000 K of color temperature. Preferably, the color temperature ranges from about 1,850 K, from about 2,500 K, from about 2,800 K, from about 3,000 K, from about 3,500 K, from about 5,000 K, or from about 5,500 K up to about 10,000 K, or up to about 8,000K, or up to about 6,500 K. In some embodiments, the light source provides about 1,850 K, about 2,500 K, about 2,800 K, about 3,000 K, about 3,500 K, about 5,000 K, about 5,500 K, about 6,500 K, about 8,000 K or about 10,000 K of color temperature.

Referring to FIG. 1, the adjusting mechanism 13 is connected to the emitting device 11. The adjusting mechanism 13 is configured to move the emitting device 11. In some embodiments of the present disclosure, the adjusting mechanism 13 is configured to change a height of the emitting device 11. In some embodiments of the present disclosure, the adjusting mechanism 13 is configured to change an elevation angle of the emitting device 11.

As shown in FIG. 1, the controller 15 coupled to the emitting device 11 and/or coupled to the adjusting mechanism 13. The controller 15 may control the overall operation of the emitting device 11.

In some embodiments of the present disclosure, the controller 15 includes a control module 151, a sensing module 153 and a control interface 155. In some embodiments of the present disclosure, the control module 151 may be implemented with a processor, a controller, an arithmetic logic unit (ALU), a digital signal processor, a microcomputer, a field programmable gate array (FPGA), a programmable logic unit (PLU), a microprocessor, etc. The control module 151 may be coupled to the emitting device 11. That is, the control module 151 may control the light-emitting operation of the emitting device 11. The control module 151 may adjust at least one of the color temperature, brightness, and color of the light emitted from the emitting device 11. The control module 151 may control the light emission operation of the emitting device 11 according to information or signals sensed by the sensing module 153. In addition, the control module 151 may be implemented to control the light-emitting operation of the emitting device 11 according to the user's switch operation. In some embodiments of the present disclosure, the control module 151 is a dimmer mounted on a wall. In addition, the control module 151 may be implemented to control the light-emitting operation of the emitting device 11 according to a control signal or information input from another device, such as the control interface 155.

The sensing module 153 may be coupled to and/or in communication with the control module 151 and/or the control interface 155. The sensing module 153 may include various types of sensors, such as an infrared sensor, a distance sensor, a gyroscope sensor, a gravity sensor, a position sensor, a proximity sensor, an illuminance sensor, or an RGB sensor (illuminance sensor), a magnetic sensor, an inertial sensor, a touch sensor, and a microphone. Further, the sensing module may detect the posture and position of the emitting device 11, the surrounding environment of the emitting device 11, or a user's motion. The sensing module 153 may transfer the data and/or information it obtained to the control module 151, and then the control module 151 may automatically control the light-emitting operation of the emitting device 11 based on the data or information from the sensing module 153. The sensing module 153 may transfer the data and/or information it obtained to the control interface 155, and the user may read such data and/or information through the control interface 155. The sensing module 153 may directly show the data and/or information it obtained to the user.

The control interface 155 may be coupled to and/or in communication with the control module 151 and/or the sensing module 153. The control interface 155 may be a remote-control unit, such as a mobile device with a control software. The control interface 155 may include a Bluetooth communication module, a BLE (Bluetooth Low Energy) communication module, a near field communication unit (Near Field Communication unit), a WLAN (Wi-Fi) communication module, a Zigbee communication module, an infrared (IrDA) data association communication module, WFD (Wi-Fi Direct) communication module, UWB (ultra wideband) communication module, and may include a communication module such as an Ant+ communication module. Further, the control interface 155 may send a command to the control module 151 so as to control the emitting device 11 and/or the adjusting mechanism 13. The control interface 155 may receive the data and/or information from the sensing module 153. That is, the emitting device 11 may receive a control command or various information related to the operation of the emitting device 11 from the control interface 155. In addition, the state information of the emitting device 11, operation information or information collected by the sensing module 153 may be provided to the control interface 155.

Moreover, the controller 15 may be coupled to or in communication with the adjusting mechanism 13. In some embodiments of the present disclosure, the control module 151 of the controller 15 is in communication with the adjusting mechanism. That is, the control module 151 may drive the adjusting mechanism 13 to move the emitting device 11 according to information or signals sensed by the sensing module 153. In addition, the user may control the adjusting mechanism 13 to move the emitting device 11 through the control interface 155 of the controller 15.

In addition, a power portion 17 may be electrically connect to the emitting device 11. The power portion 17 is configured to supply operating power of the emitting device 11. In some embodiments of the present disclosure, the power portion 17 may include a battery. In some embodiments of the present disclosure, the power portion 17 may be connected to the emitting device 11 through a power cable. In some embodiments of the present disclosure, the power portion 17 may include a waterproof adjustable power source.

Figure 2:
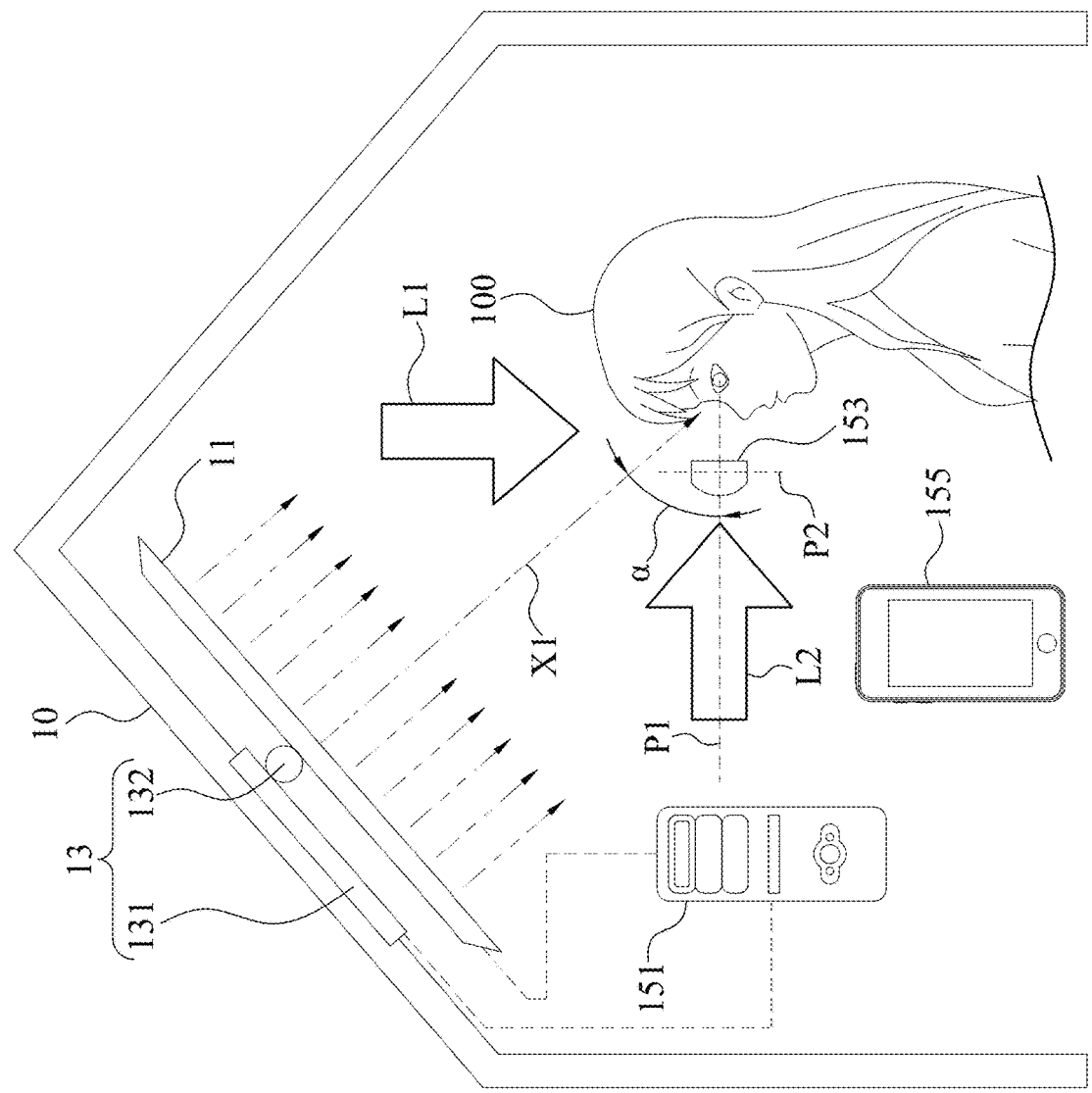
FIG. 2 is a schematic view of a light system in an ambient environment in accordance with an embodiment of the instant disclosure.

FIG. 2 is a schematic view of a light system 1 in an ambient environment 10 in accordance with an embodiment of the instant disclosure. As shown in FIG. 2, the emitting device 11 is arranged in the ambient environment 10 and provides a light into the ambient environment 10. In some embodiments of the present disclosure, the ambient light in the ambient environment 10 includes the light provided by the emitting device 11. In some embodiments of the present disclosure, the ambient light in the ambient environment includes the light provided by the emitting device mixed with the original light in the ambient environment 10.

A subject 100 is in the ambient environment 10 and exposed to the ambient light. That is, the light emitted from the emitting device 11 may impinge on the subject 100. In some embodiments of the present disclosure, the subject 100 sits and receives such light. In some embodiments of the present disclosure, the subject 100 stands and receives such light. In some embodiments of the present disclosure, the subject lies down and receives such light. In some embodiments of the present disclosure, the emitting device 11 may provide light having a total vertical illuminance L1 and/or a vertical illuminance L1 of the green light or the green spectral component of at least about 2,000 lux, about 2,500 lux, about 3,000 lux, about 3600 lux, about 4,000 lux, about 4,400 lux or about 4,800 lux. The subject 100 may be exposed to the ambient light with vertical illuminance L1 of at least about 2,000 lux, about 2,500 lux, about 3,000 lux, about 3600 lux, about 4,000 lux, about 4400 lux or about 4800 lux. In some embodiments of the present disclosure, the emitting device 11 may provide light having a total vertical illuminance L1 and/or a vertical illuminance L1 of the green light or the green spectral component of about 4000 lux to about 4400 lux. The subject 100 may be exposed to the ambient light with vertical illuminance L1 of about 4000 lux to about 4400 lux. In some embodiments of the present disclosure, the emitting device 11 may provide light having a total vertical illuminance L1 and/or a vertical illuminance L1 of the green light or the green spectral component of about 3600 lux to about 4800 lux. The subject 100 may be exposed to the ambient light with vertical illuminance L1 of about 3600 lux to about 4800 lux. In some embodiments, the total vertical illuminance L1 and/or the vertical illuminance L1 of the green light or the green spectral component is measured at the ear, eye, or top-of-the-head height level of the subject 100. That is, the total vertical illuminance L1 may be the amount of light falling on a horizontal surface or plane P1 at the ear, eye, or top-of-the-head height level of the subject 100. The vertical illuminance L1 of the green light or the green spectral component may be the amount of green light falling on a horizontal surface or plane P1 at the ear, eye, or top-of-the-head height level of the subject 100.

In some embodiments of the present disclosure, the emitting device 11 may provide light having a total horizontal illuminance and/or a horizontal illuminance L2 of the green light or the green spectral component of at least about 15 lux, about 300 lux, about 350 lux, about 400 lux, about 500 lux, about 750 lux, about 1000 lux, about 1500 lux, about 2000 lux, about 2200 lux, about 2500 lux or about 2800 lux. The subject 100 may be exposed to the ambient light with horizontal illuminance L2 of at least 15 lux, about 300 lux, about 350 lux, about 400 lux, about 500 lux, about 750 lux, about 1000 lux, about 1500 lux, about 2000 lux, about 2200 lux, about 2500 lux or about 2800 lux. In some embodiments of the present disclosure, the emitting device 11 may provide light having a total horizontal illuminance L2 and/or a horizontal illuminance L2 of the green light or the green spectral component of about 2200 lux to about 2800 lux. The subject 100 may be exposed to the ambient light with vertical illuminance L2 of about 2200 lux to about 2800 lux. In some embodiments, the total horizontal illuminance L2 and/or the horizontal illuminance L2 of the green light or the green spectral component is measured at the ear, eye, or top-of-the-head height level of the subject 100. That is, the total horizontal illuminance L2 may be the amount of light falling on a vertical surface or plane P2 at the ear, eye, or top-of-the-head height level of the subject 100. The horizontal illuminance L2 of the green light or the green spectral component may be the amount of green light falling on a vertical surface or plane P2 at the ear, eye, or top-of-the-head height level of the subject 100.

In some embodiments of the present disclosure, the emitting device 11 is configured at an angle of more than about 30 degrees formed between the emitting device 11 and the subject 100. In some embodiments of the present disclosure, the angle is formed between the emitting device and the ear, eye, or top-of-the-head height level of the subject 100. In some embodiments, the angle ranges from about 30 degrees, or from about 40 degrees, or from about 45 degrees up to about 90 degrees, or up to about 80 degrees, or up to about 60 degrees. That is, the light emitted from the emitting device 11 to the subject 100 and a plane P1 at eye level of a subject 100 forms an angle and the angle ranges from about 30 degrees, or from about 40 degrees, or from about 45 degrees up to about 90 degrees, or up to about 80 degrees, or up to about 60 degrees. In some embodiments of the present disclosure, the angle of the light emitted from the emitting device 11 to the subject 100 and a plane P1 at eye level of a subject 100 is about 45 degrees. Thus, the light from the emitting device 11 to the subject 100 includes an optical axis, and the optical axis and the plane P1 at eye level of a subject 100 forms an angle α and the angle α ranges from about 30 degrees, or from about 40 degrees, or from about 45 degrees up to about 90 degrees, or up to about 80 degrees, or up to about 60 degrees. In some embodiments of the present disclosure, the angle α between the optical axis of the light from the emitting device 11 to the subject 100 and the plane P1 at eye level of a subject 100 is about 45 degrees. In other words, a line X1 extending from the emitting device 11 to the subject 100 and the plane P1 at eye level of a subject 100 forms an angle α and the angle α ranges from about 30 degrees, or from about 40 degrees, or from about 45 degrees up to about 90 degrees, or up to about 80 degrees, or up to about 60 degrees. In some embodiments of the present disclosure, the angle α between the line X1 extending from the emitting device 11 to the subject 100 and the plane P1 at eye level of a subject 100 is about 45 degrees. The line X1 extending from the emitting device 11 to the subject 100 may include the optical axis of the light emitted from the emitting device 11.

Referring to FIG. 2, the adjusting mechanism 13 may include a lifting table 131 and a head 132. The emitting device 11 may be mounted on the head 132 and the head 132 may be connected to the lifting table 131. The head 132 is configured to change an angle of elevation of the emitting device 11. The lifting table 131 is configured to change a height of the emitting device. That is, the illuminance of the light provided by the emitting device 11 and/or the optical axis of the light provided by the emitting device 11 may be changed by the adjusting mechanism 13.

Further, as shown in FIG. 2, the sensing module 153 may be positioned to be adjacent to the ear, eye or the top of the head of the subject 100. In some embodiments of the present disclosure, the sensing module 153 is configured to detect the total vertical illuminance L1 and/or a horizontal illuminance L2 of the green light or the green spectral component at the ear, eye, or top-of-the-head height level of the subject 100.

The control module 151 may be connected to or in communication with the adjusting mechanism 13 and the emitting device 11. The control module 151 may change the position of the emitting device 11 by driving the adjusting mechanism 13 and control the emitting operation of the emitting device 11. Thus, the angle between the optical axis of the light and the plane P1 at eye level of a subject 100 and the illuminance of the green light or the green spectral component at the ear, eye, or top-of-the-head height level of the subject 100 may be changed by the control module 151. In some embodiments of the present disclosure, the control module 151 is connected to or in communication with sensing module 153, and the control module 151 drives the adjusting mechanism 13 and/or control the emitting device according to the information/data from the sensing module 153. In some embodiments of the present disclosure, the control module 151 is connected to or in communication with control interface 155, and the control module 151 drives the adjusting mechanism 13 and/or control the emitting device according to the command from the control interface 155. In some embodiments of the present disclosure, the control interface 155 is connected to or in communication with sensing module 153, and the subject 100 may read the information/data collected by the sensing module 153 through the control interface 155.

Figure 3:
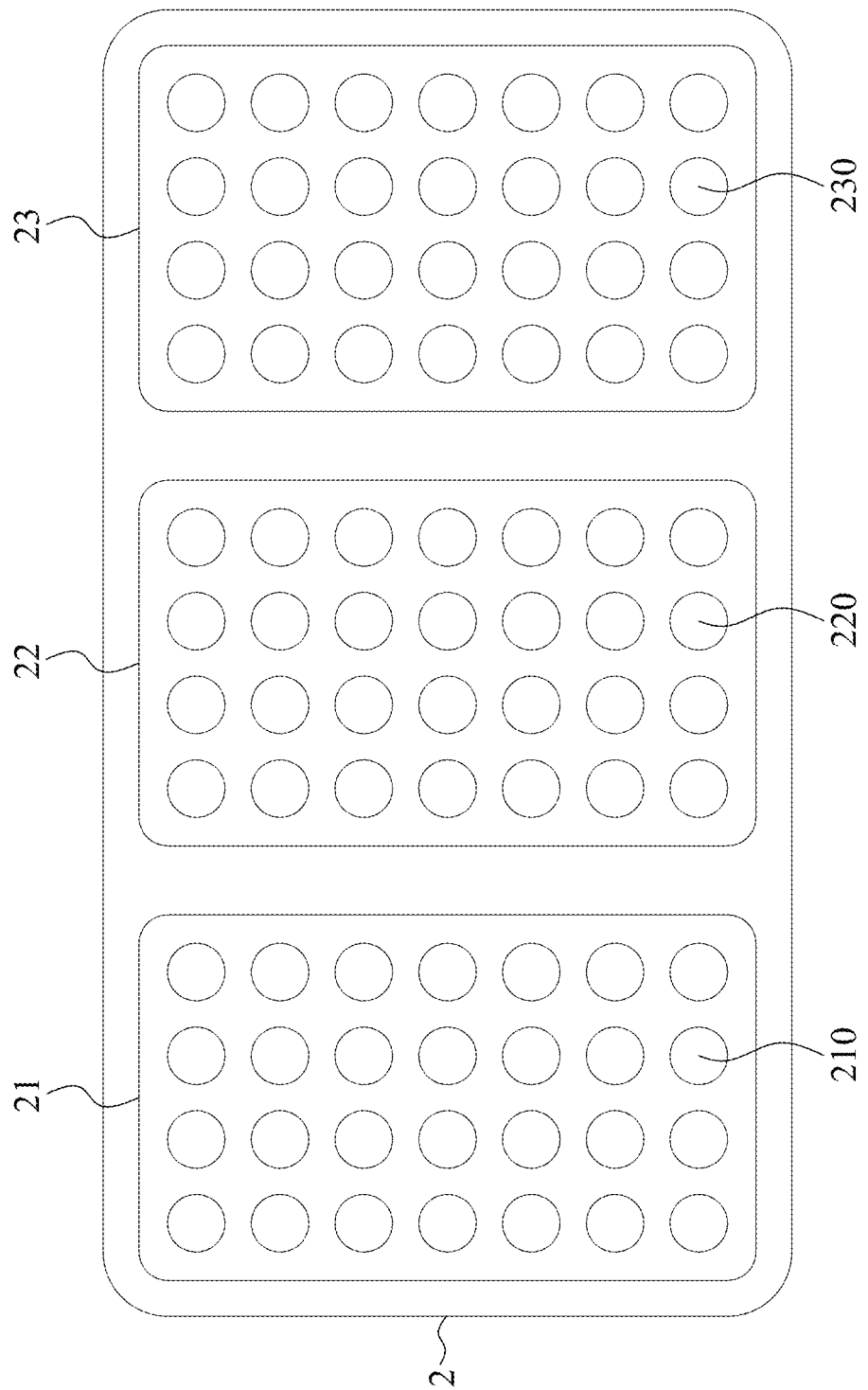
FIG. 3 is a schematic view of an emitting device in accordance with an embodiment of the instant disclosure.

FIG. 3 is a schematic view of an emitting device 2 in accordance with an embodiment of the instant disclosure. The emitting device 2 is the same as, or similar to, the emitting device 11. The emitting device 2 may include a red light LED group 21, a green light LED group 22 and a blue light LED group 23. The red light LED 21 group may include a plurality of red light LED units 210. The green light LED group 22 may include a plurality of green light LED units 220. The blue light LED group 23 may include a plurality of blue light LED units 230. The number of the red light LED units 210 is N. The number of the green light LED 220 units is M. The number of the blue light LED units 230 is L. Further, N, M and L are positive integers. In some embodiments of the present disclosure, $0.2 \leq M/(N+M+L) \leq 0.6$. That is, the light emitted by the emitting device may include green light or green spectral component of a light which ranges from 20% to 60%. In some embodiments of the present disclosure, $0.25 \leq M/(N+M+L) \leq 0.45$. That is, the light emitted by the emitting device may include green light or green spectral component of a light which ranges from 25% to 45%. In some embodiments of the present disclosure, $0.4 \leq M/(N+M+L)$. That is, the light emitted by the emitting device may include at least 40% green light or green spectral component of a light. In some embodiments of the present disclosure, the size of the emitting device 2 is 300 mm×1200 mm. In some embodiments of the present disclosure, the size of the emitting device 2 is 600 mm×600 mm.

Figure 4:
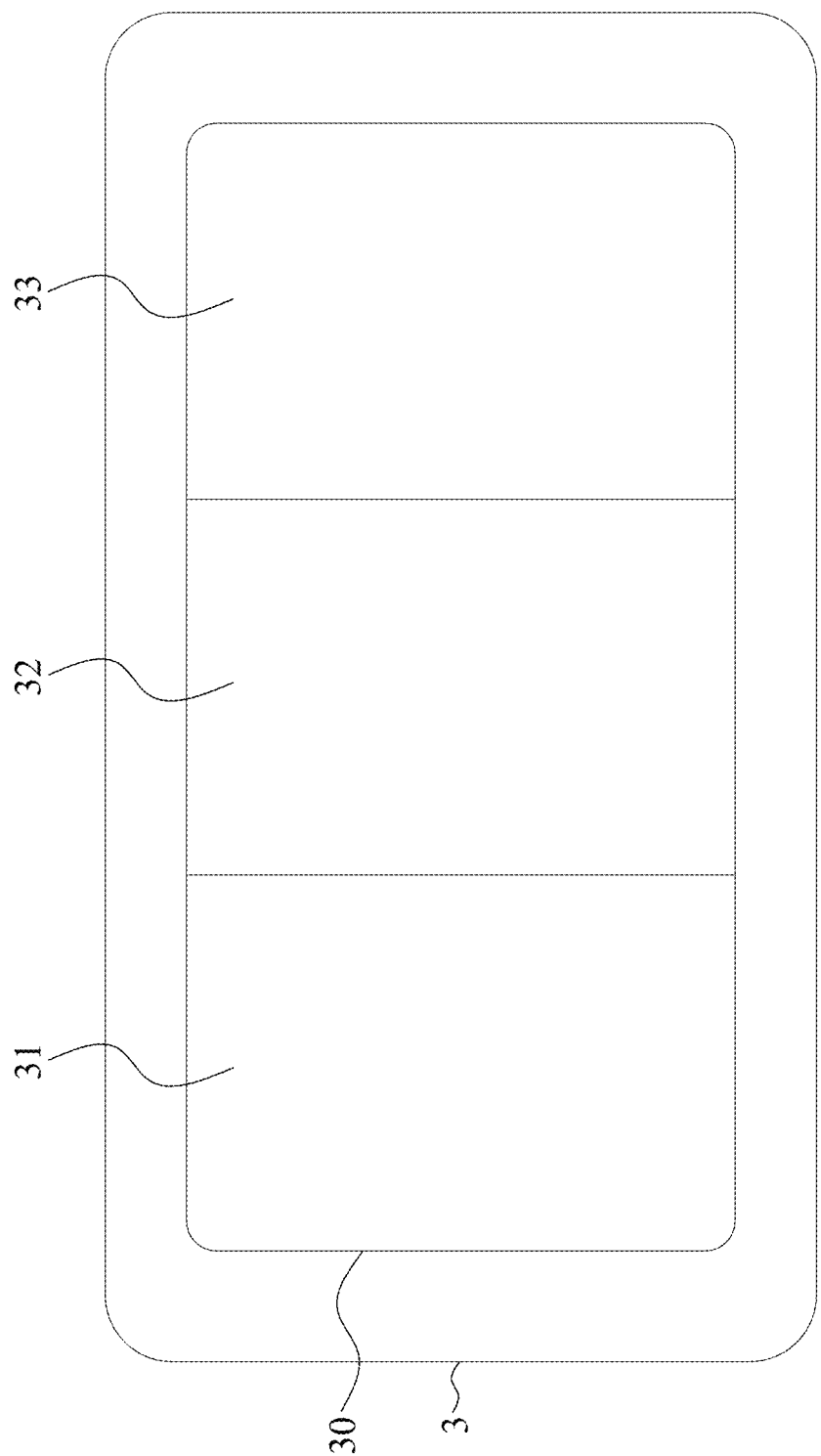
FIG. 4 is a schematic view of an emitting device in accordance with an embodiment of the instant disclosure.
Figure 5:
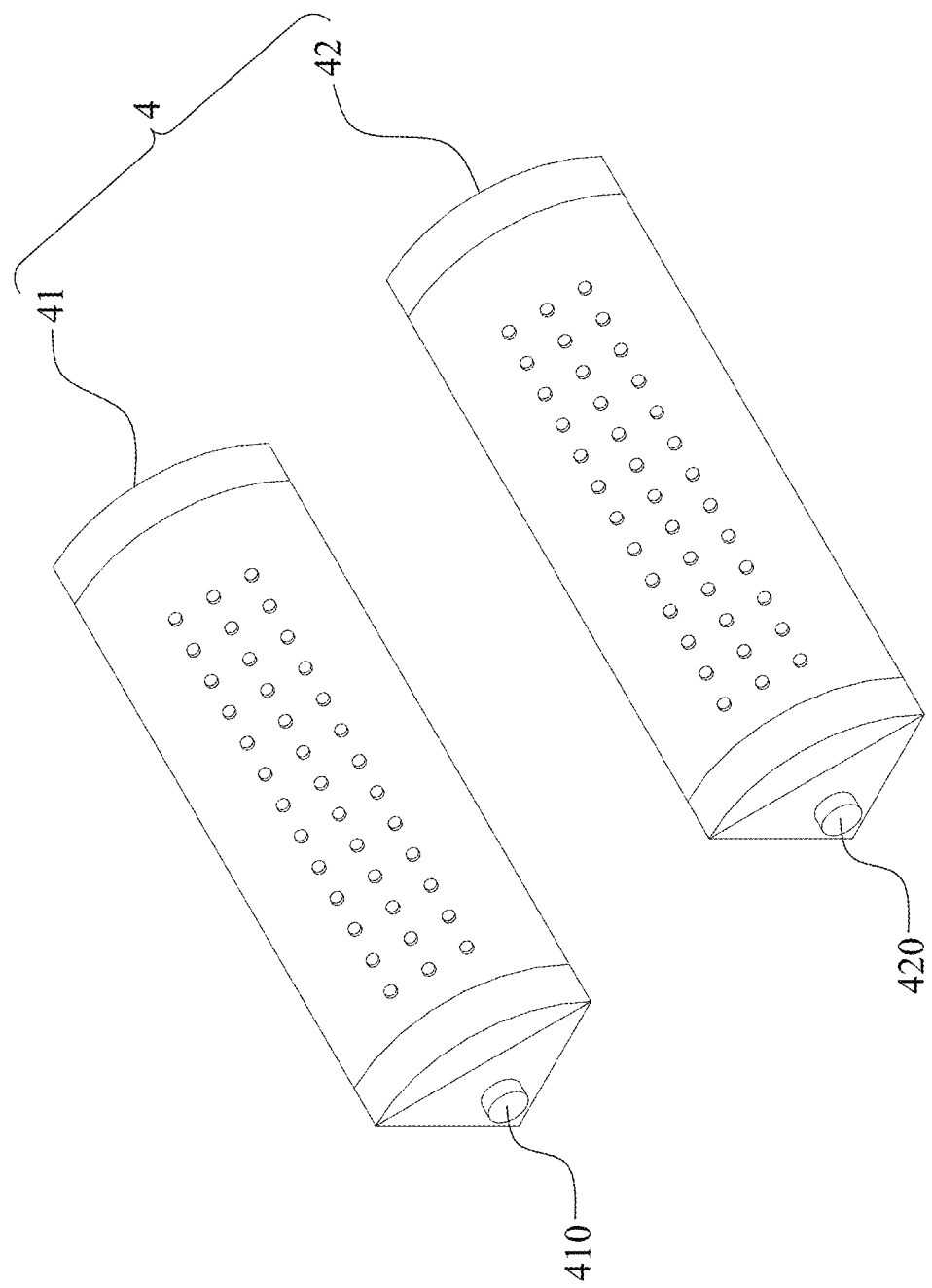
FIG. 5 is a schematic view of an emitting device in accordance with an embodiment of the instant disclosure.

FIG. 4 is a schematic view of an emitting device 3 in accordance with an embodiment of the instant disclosure. The emitting device 3 is the same as, or similar to, the emitting device 11. The emitting device 3 may include an optical filter 30 having a red light transition region 31, a green light transition region 32 and a blue light transition region 33. The area of the red light transition region 31 is P. The area of the green light transition region 32 is Q. The area of the blue light transition region is R. Further, P, Q and R are positive integers. In some embodiments of the present disclosure, $0.2 \leq Q/(P+Q+R) \leq 0.6$. That is, the light emitted by the emitting device may include green light or green spectral component of a light which ranges from 20% to 60%. In some embodiments of the present disclosure, $0.25 \leq Q/(P+Q+R) \leq 0.45$. That is, the light emitted by the emitting device may include green light or green spectral component of a light which ranges from 25% to 45%. In some embodiments of the present disclosure, $0.4 \leq Q/(P+Q+R)$. That is, the light emitted by the emitting device may include at least 40% green light or green spectral component of a light. In some embodiments of the present disclosure, the size of the emitting device 2 is 300 mm×1200 mm. In some embodiments of the present disclosure, the size of the emitting device 2 is 600 mm×600 mm.

FIG. 4 is a schematic view of an emitting device 4 in accordance with an embodiment of the instant disclosure. The emitting device 4 is the same as, or similar to, the emitting device 11. The emitting device 4 may include brick lamps 41 and 42. The brick lamp 41 may include electrical connections 410. The brick lamp 42 may include electrical connections 420. The brick lamps 41 and 42 may be electrically connected to each other through the electrical connections 410 and/or 420. That is, the brick lamps 41 and 42 are configured to be tiled with each other. Thus, the brick lamp 41, 42 can be used with different styles of ambient environments.

Figure 6:
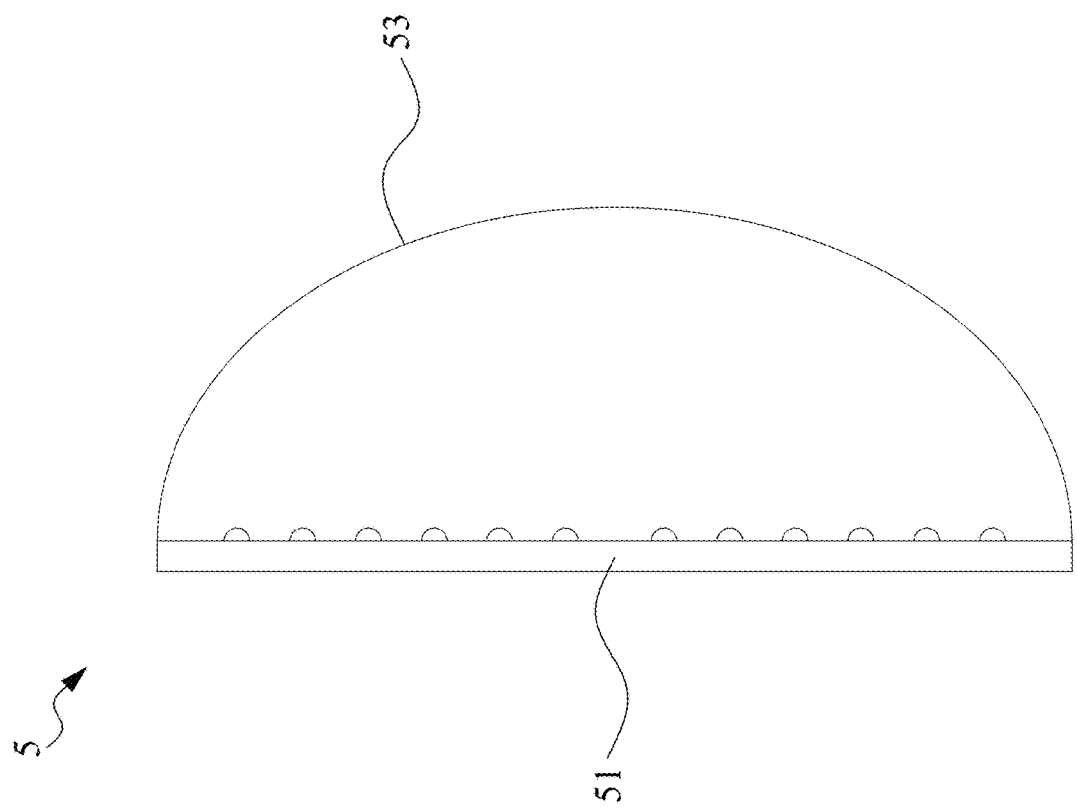
FIG. 6 is a schematic view of an emitting device in accordance with an embodiment of the instant disclosure.

FIG. 6 is a schematic view of an emitting device 5 in accordance with an embodiment of the instant disclosure. The emitting device 5 is the same as, or similar to, the emitting device 11. The emitting device 5 may include a light source 51 and a diffusing fitting 53. The diffusing fitting 53 is configured to diffuse the light emitted from the light source 51.

Figure 7:
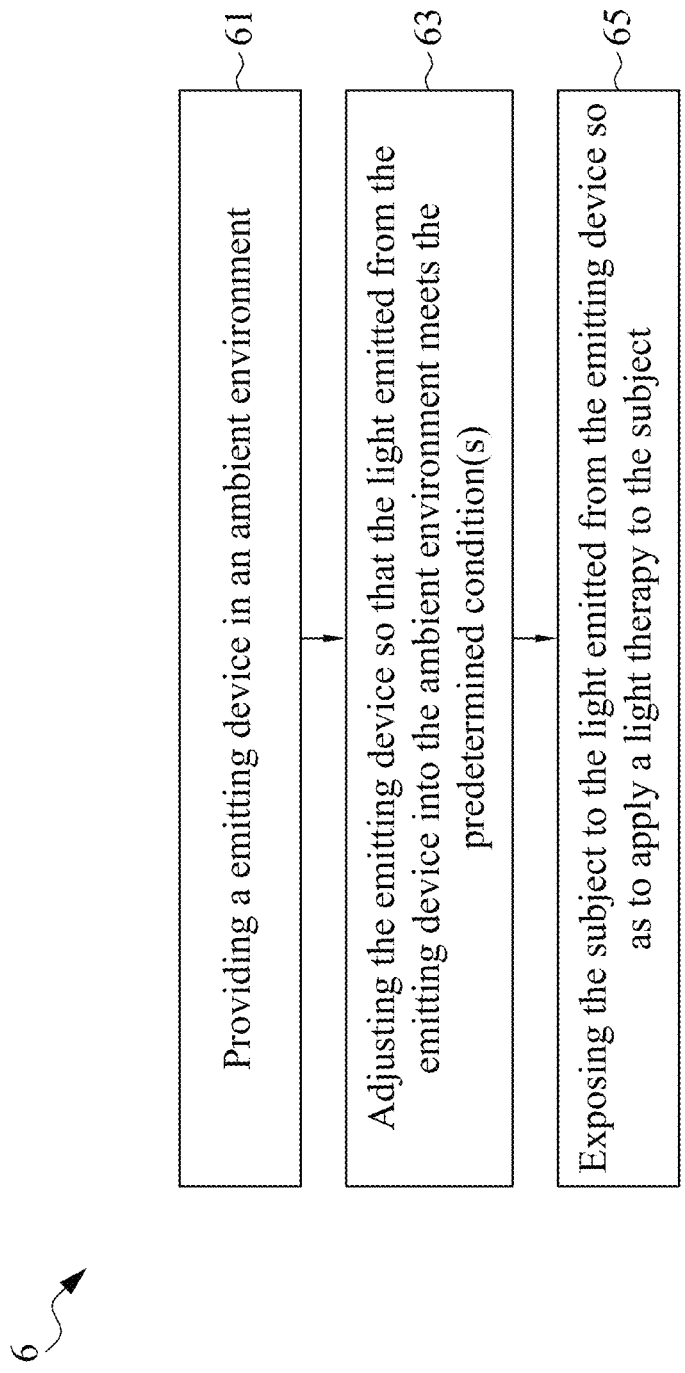
FIG. 7 is a flow chart representing exemplary operations of the method for providing ambient lighting for improving sleeping disorders, cognition and/or neurological disorders in a subject.

FIG. 7 is a flow chart representing exemplary operations of the method 6 for providing ambient lighting for improving sleeping disorders, cognition and/or neurological disorders in a subject. As stated above, light therapy is a way to treat seasonal affective disorder (SAD) and certain other conditions by exposure to artificial light. Light therapy is thought to affect brain chemicals linked to mood and sleep while easing SAD symptoms. The method 6 is related to the operations for providing an ambient environment with a light system, in which the light therapy could be performed.

In operation 61, an emitting device, which is the same as, or similar to, the emitting device 11, is provided in an ambient environment. For example, the emitting device may provide a light source providing at least 20% (preferably at least 30%) green light or green spectral component of a light. Ratio of the green light can be calculated by defining the areas of the spectrum of the green regions relative to the entire spectrums, and the emitting device provides at least 1,850 K, at least 2,500 K, at least 2,800 K, at least 3,000 K, at least 3,500 K, at least 5,000 K, at least 5,500 K, at least 6,500 K, at least 8,000 K or at least 10,000 K of color temperature.

In operation 63, the emitting device is controlled and/or adjusted so that an optical axis of the light emitted from the emitting device and/or an illuminance of the light provided from the emitting device meet the predetermined conditions.

As stated above, an angle between the optical axis of the light emitted from the emitting device to the subject in the ambient environment and the plane at eye level of the subject 100 ranges from about 30 degrees, or from about 40 degrees, or from about 45 degrees up to about 90 degrees, or up to about 80 degrees, or up to about 60 degrees. In some embodiments of the present disclosure, the emitting device is moved by an adjusting mechanism so that the light of the emitting device meets the above condition. In some embodiments of the present disclosure, the subject controls the adjusting mechanism to change the height of the emitting device and/or change the angle of elevation of the emitting device so that the light of the emitting device meets the above condition.

Moreover, the subject in the ambient environment may be exposed to the ambient light with vertical illuminance of about 3600 lux to about 4800 lux and/or horizontal illuminance of about 2200 lux to 2800 lux, and the vertical illuminance and/or a vertical illuminance of the green light or the green spectral component and the horizontal illuminance and/or a horizontal illuminance of the green light or the green spectral component is measured at the ear, eye, or top-of-the-head height level of the subject. In some embodiments of the present disclosure, the brightness of the emitting device is controlled by the controller so that the vertical illuminance of the light on the subject meets the above condition. In some embodiments of the present disclosure, the emitting device is moved by an adjusting mechanism so that the vertical illuminance of the light on the subject meets the above condition.

In operation 65, after the light emitted from the emitting device into the ambient environment is adjusted to meet the predetermined condition(s), the subject may be exposed to the light and the light system may apply a light therapy to the subject.

EXAMPLES

Testing and Validation 1.1 Study Design

This study followed a single-blind longitudinal-group experimental design using a between-group trial, with group assignment being determined by acceptance order. Diagnosis of dementia requires a history of cognitive decline and impaired daily activities, with corroboration from the primary caregiver and nursing staff in nursing homes. Moreover, it requires mental status examination by a clinician to determine impairments in memory, language, attention, visuospatial cognition such as spatial orientation, executive function, and mood. Participants in the experimental and comparison groups were exposed to ambient bright light (2500 lux) and general lighting, respectively.

1.2. Participants

The required sample size was calculated using G*Power 3.1 computer software, yielding an estimate of 20 participants; the data were analyzed using analysis of variance (ANOVA) with the conditions set at statistical significances of $\alpha=0.05$ and $\beta=0.2$ with an effect size of $f=0.39$. Participants were selected based on the following inclusion criteria: 1) diagnosed with dementia according to the Diagnostic and Statistical Manual of Mental Disorders, fifth edition (DSM-5); 2) aged between 60 and 95 years; 3) consented to participate in the study, per the participants or their guardians; and 4) willing to participate in the group. Participants were excluded if 1) they had adverse reactions to light, such as systemic lupus erythematosus, epilepsy, blindness, retinal detachment, or macular degeneration; 2) when using an accelerometer, the data on sleep disturbances that were collected at baseline showed sleep efficiency >80%, <4 nocturnal awakenings, fewer than three nights per week with sleep disturbances, or disruptions lasting less than one month; and 3) had a measured score of <3 points on the Mini-Mental State Examination (MMSE) or were unable to express self-intentions verbally.

Figure 8:
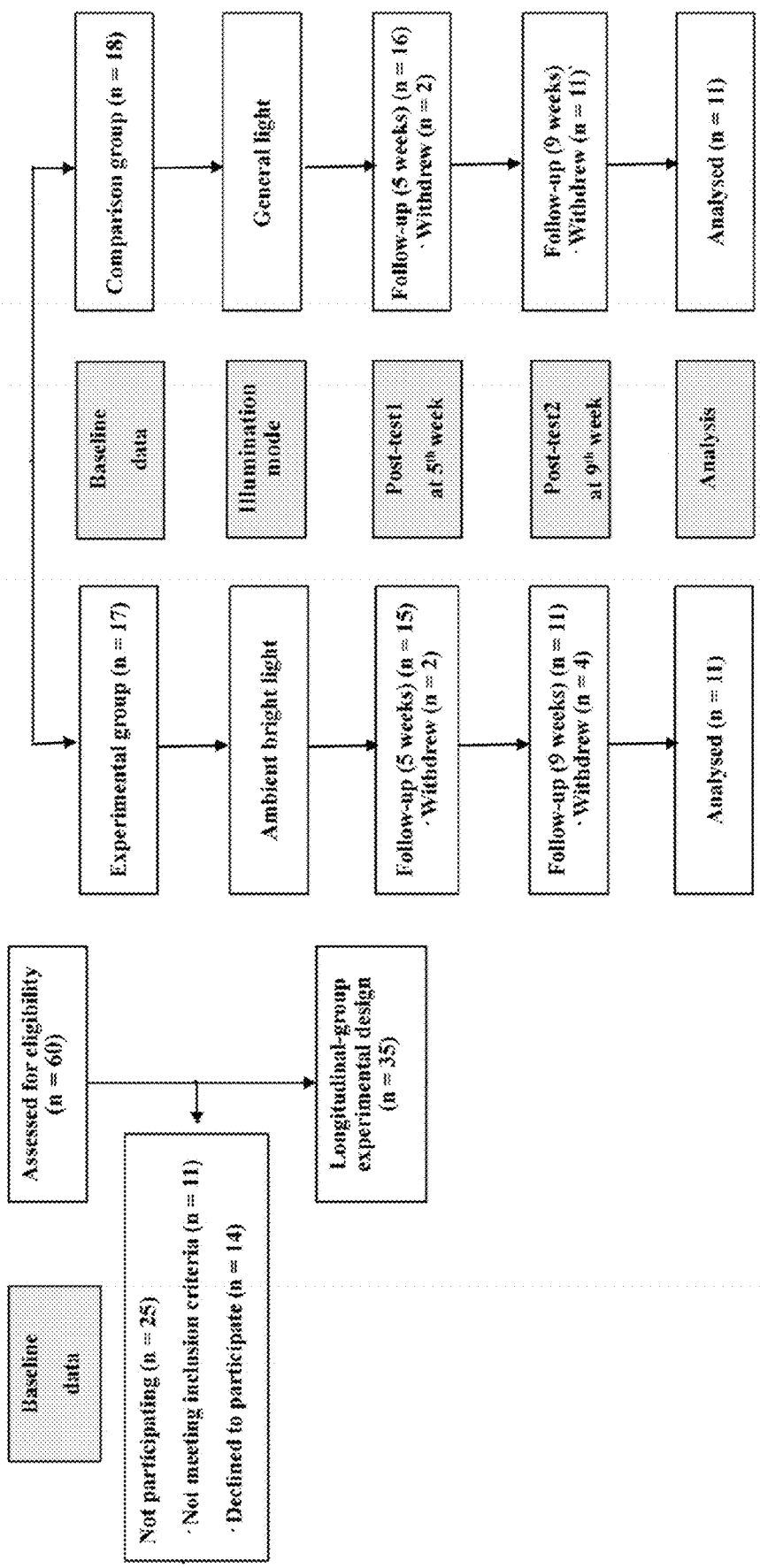
FIG. 8 is a flow chart of participant recruitment.

Among 60 eligible patients, 11 did not meet the inclusion criteria and 14 declined to participate. Accordingly, we included 35 patients and consecutively allocated them to the experimental (n=17) and comparison (n=18) groups. Among them, 13 patients withdrew from the study for the following reasons: unavailability of family members to accompany them to daily therapy (n=9), suffering from pneumonia or leg injuries (n=2), and inability to integrate into the group (n=2). Finally, only 22 patients completed the entire study (FIG. 8). The patients were taken to the experimental site for five days a week.

1.3. Experimental Group: the Ambient Bright Light Therapy Model

The experimental group was exposed to ambient bright light with horizontal and vertical illuminations according to the present application of 2500-2600 lux and 4000-4400 lux, respectively, from a panel light (QBX801K99) in a special room. Ambient lights were placed on the ceiling within a 45° visual field with full-spectrum light (≥2500 lux) to provide exposure (FIG. 9A). Participants were exposed to ambient bright light for at least 60 min/day from 9 AM to 10 AM, Monday through Friday, over eight weeks. In total, the participants were exposed to ambient bright light for 40 h, with group participation. The horizontal illumination started at 500 lux, which was increased daily by 500 lux until it reached and was maintained at 2500 lux. Participants were seated on a chair approximately 1.2 m away from the artificial source of ambient light at eye level. The CL-500A illuminometer was used to standardize ambient bright light at 2500 lux, with the same parameters being applied throughout the study period. The surrounding environment lights were switched off and the curtains drawn to enhance the artificial ambient exposure. Moreover, the special aluminum windows completely shielded the participants from exposure to external light. Consistency of the light exposure with the experimental parameters was ensured using a light measuring instrument. To reduce sunlight interference factors, the participants were provided with sunglasses to wear before going outdoors.

1.4. Comparison Group: General Light Model

Participants in the comparison group were exposed to general lighting, with horizontal and vertical illumination at 114-307 lux and 600-800 lux, respectively (FIG. 9B). There were placed in a room without windows; moreover, some rooms had curtains to ensure that the illumination remained constant throughout.

1.5 Feasibility: Retention, Attendance, and Adverse Events

All the participants from the experimental and comparison groups completed profile tracing. Thirty-five participants completed the baseline assessment, and 29 and 22 participants completed the $5^{th}$. and $9^{th}$. week assessments, respectively, for a retention rate of 64.7% in the experimental group and 61.1% in the comparison group. The attendance rate was 93% in the experimental group and 75% in the comparison group. No adverse effects were observed (e.g., fall, injury, eye injury, headache, and dizziness) during the 8 weeks of light therapy.

2.1. Instruments and Outcome Measures

In this application, demographic data, as well as sleep efficiency, sleep time, number of nighttime awakenings, awakening time, and circadian rhythms were collected and determined using an accelerometer. Data were collected at baseline and in the fifth and ninth week. Data collectors were blinded to the participants. In addition, behavioral and psychological symptoms of dementia (BPSD) were determined using the Neuropsychiatric Inventory (NPI), and cognitive function outcomes were obtained using the MMSE. The NPI data were obtained by interviewing the corresponding caregivers and nursing home staff, while the researchers directly obtained the MMSE data.

2.2.1. Participant Demographic Data

Demographic data included gender, age, education level, marital status, sleep pattern, dementia type, dementia severity, dementia source, total physical activity in the day, and medication use (benzodiazepines, antidepressants, antipsychotics, and antidementia drugs).

2.2.2. Defined Daily Dose (DDD)

According to the World Health Organization (WHO), the defined daily dose (DDD) is the assumed average maintenance dose per day for a drug in adults. The DDD only represents a measurement unit, with drug usage (in DDDs) being calculated as the total drug dose by the DDD. Assessments were performed at baseline and in the fifth and ninth week to monitor the impact of drug changes on our findings.

2.2.3. Validity and Reliability of the Accelerometer

Regarding sleep measurement using an accelerometer, hand, rather than body, movements are detected along three axes. Specifically, accelerometer activity is recorded as the acceleration along the x-, y-, and z-axes of three-dimensional space. Compared with polysomnography, accelerometers have higher and lower sensitivity and specificity, respectively; additionally, they can detect sleep disturbances, circadian rhythms, and total physical activity in the day.

Accelerometer-monitored sleep disturbance data were recorded using an accelerometer. Compared with sleep logs of older adults with dementia, with the between-measurement error value being <30 min, and the accelerometer (XA-5, Taipei, Taiwan) had an 80% accuracy level. The accelerometer (XA-5) was worn around the wrist to continuously record actigraphic data for ≥3 days at baseline using the KY laboratory software package (http://xds.ym.edu.tw/sl). The device contains a piezoelectric linear accelerometer and associated circuitry for recording movement intensity and movement associated with physical activity, yielding three variables: total physical activity (average of all activity movements per hour), maximum activity (the largest and/or maximum movement per hour), and average activity (average movement per hour).

2.2.4. Sleep Pattern

According to the reports of caregivers and nursing staff in the nursing homes, sleep and wake times were observed for a week. Additionally, patterns were classified as advanced sleep-wake phase disorder, delayed sleep-wake phase disorder (DSWPD), irregular sleep-wake rhythm disorder, or a sleep-wake rhythm and accelerometer-monitored sleep pattern data were recorded using an accelerometer. Compared with sleep logs of older adults with dementia, the between-measurement error value was <30 min. The accelerometer (XA-5, Taipei, Taiwan) was worn around the wrist to continuously record actigraphic data for ≥3 days at baseline using the KY laboratory software package.

2.2.5. Mini-Mental State Examination

The MMSE was developed by Folstein et al. for quantitative dementia-related cognitive screening, ranging from 0

(worst) to 30 (best). It has good test-retest reliability (0.80e0.95), sensitivity, and specificity for detecting mild dementia stages. In this application, the MMSE showed adequate overall internal consistency ($\alpha=0.85$). The MMSE is categorized into orientation [e.g., orientation questions, five each for time and place (10 points)], registration [e.g., three-word registration and 1-min recall (3 points)], attention and calculation [e.g., assessed either by serial subtraction of 7 from 100 or serial subtraction of 3 from 20 (5 points)], recall [e.g., three-item recall test for memory (3 points)], and language, visuospatial construction [assessed by a three-stage command, repetition, naming, reading comprehension, and writing (8 points) and copying two intersecting pentagons (1 point)] (Graf et al., 2001). Cronbach's a coefficients for older adults with dementia were 0.81 and 0.88 for the pretest and posttest, respectively. The MMSE was used to assess the severity of dementia. Scores of $\geq 21$ indicate the presence of mild dementia, 11-20 indicate moderate dementia, and 0-10 indicate severe dementia.

2.2.6 Neuropsychiatric Inventory

The NPI was developed by Cummings et al. (1994) (see also Connor et al., 2008; Lai, 2014) to assess dementia-related psychopathology and neuropsychiatric behaviors. The NPI includes four domains: emotional symptoms (e.g., dysphoria, anxiety, apathy, euphoria, and irritability), psychiatric symptoms (e.g., delusions and hallucinations), behavioral problems (e.g., agitation, disinhibition, aberrant motor behavior, appetite, and eating abnormalities), and sleep disturbances (e.g., nighttime behavioral disturbances) (Connor et al., 2008). The NPI shows good content validity, concurrent validity, and interrater reliability. The caregivers were asked to rate the frequency of the symptoms of each disturbance on a scale of 1 (occasionally or less than once a week) to 4 (very frequently, more than once a day, or continuously). The rating of the symptom severity was 1, 2, or 3 for mild, moderate, or severe, respectively. The total score ranged from 0 to 144 points, where a higher score reflects a more severe level of BPSD. The NPI subdomains were significantly correlated with the domains of behavioral disturbances and the Hamilton Rating Scale for Depression. Interrater reliability ranged from 93.6 to 100%, depending on the subdomain, and test-retest reliability was also high: r (20)=0.79 (Cummings et al., 1994; Connor et al., 2008; Lai, 2014; Cloak and Al Khalili, 2021). In this study, the NPI exhibited adequate overall internal consistency (a=0.66). Cronbach's a coefficients for the older adults with dementia were 0.56 and 0.75 for the pretest and posttest, respectively.

2.2.8 Statistical Analyses

Statistical analyses were performed using SPSS 24.0 statistical software. Regarding demographic characteristics, gender, education level, marital status, sleep pattern, dementia type, and dementia source were considered. The descriptive statistics at baseline and on the fifth and ninth week were calculated to examine whether demographic characteristics were affected by the loss of any participant. Descriptive statistics are presented as the number of cases (n), percentage (%), and mean and standard error, according to the group. The primary pretest-posttest analyses were based on the intention to treat (ITT) sample. For inferential statistics, nonparametric statistics (the chi-square and ManneWhitney U tests) for between- and within-group comparisons of pre- and post-intervention profiles were used. Specifically, the ManneWhitney U test was used to assess within-group differences in age and medication (benzodiazepines, antidepressants, antipsychotics, and antidementia drugs) at baseline. An independent samples t-test was used to assess sleep efficiency, sleep time, awakening time, number of nighttime awakenings, circadian rhythms, and total physical activity during the day. The DDD was used as the unit of drug usage. Given the possible consequences of repeated measurements, generalized estimating equations (GEE) were used for between group comparisons to assess the intervention effects. Improvements in the outcomes over time in both groups were analyzed using GEE with an exchangeable working correlation matrix. A robust standard error was used to calculate statistical significance. The applicant tested for the main effects of group (experimental and control groups) and time points (baseline, fifth week, and ninth week), as well as their interaction (group time point). A significant interaction effect indicated a significant between-group difference in changes over time. Benzodiazepines and total physical activity during the day were included as covariates in the GEE.

3. Sleep Disturbances of Older Adults with Dementia

3.1. Demographic and Clinical Characteristics

FIG. 8 presents the study's flowchart. In this study, 35, 31, and 22 participants completed the baseline, 5-week, and 9-week assessments, respectively. The retention rates in the experimental and comparison groups were 64.7% and 61.1%, respectively. There was no significant between-group difference in the demographic characteristics (education level, marital status, sleep pattern, dementia severity, dementia type, and source) at baseline and in the fifth and ninth week. This finding indicated homogenous distribution across the participants. However, there was a significant between-group difference in gender, with males comprising 5.9% and 33% of patients in the experimental and comparison groups, respectively (P<0.05). Most participants were females. Further, there was no significant between-group difference in age, education level, marital status, sleep pattern, dementia severity, dementia type, source, medication, and total physical activity in the day, with the mean age of the experimental and comparison groups being 83.9 years (SD=7.1 years) and 80.2 years (SD=7.2 years), respectively. This indicated homogenous distribution of the participants.

3.2. Effect of Bright Ambient Light on Sleep Disturbances

As shown in Table 1, independent samples t-tests were used to analyze the participants' sleep disturbances. There were no significant between-group differences in sleep efficiency, sleep time, awakening time, and total physical activity in the day. However, there was a significant between-group difference in the number of nighttime awakenings (5.6 and 7.5 in the experimental and comparison groups, respectively, P<0.05). This indicates a homogenous distribution of the participants' sleep disturbances.

TABLE 1

| Step | Sleep efficiency[a] mean | | | Wald $X^{2h}/T^i$ P value | sleep time[b] mean | | | Wald $X^{2h}/Z^i$ P value |
|---|---|---|---|---|---|---|---|---|
| | Exp[e] | Con[f] | Diff[g] | | Exp[f] | Con[g] | Diff[h] | |
| Week 0[j] | 55.8% | 60.0% | -4.2% | -0.58[i] 0.56 | 322.4 | 338.3 | -15.9 | -0.33[i] 0.73 |
| Week 5[th,k] | 79.2% | 50.5% | 28.7% | | 463.2 | 287.29 | 152.9 | |
| Week 5[th,L] | 76.9% | 51.5% | 25.4% | | 450.3 | 297.4 | 152.9 | |
| Week 9[th,M] | 76.5% | 54.9% | 21.6% | | 457.0 | 320.1 | 136.9 | |
| Week 9[th,N] | 76.0% | 56.7% | 19.3% | | 446.1 | 333.5 | 112.6 | |
| Week 5-0 | 23.4% | -9.5% | 32.9% | 18.85 <0.001*** | 140.8 | -41.1 | 156.9 | 11.5 0.001*** |
| Week 9-0 | 20.7% | -5.1% | 25.8% | 9.91 0.002** | 134.6 | -5.0 | 116.6 | 6.94 0.008** |
| Week 9-5 | -2.7% | 4.4% | -7.1% | 0.94 0.33 | -6.2 | 32.8 | -16.0 | 0.01 0.91 |

| Step | Awakening time[c] mean | | | Wald $X^{2h}/Z^i$ P value | Number of night time awakenings[d] mean | | | Wald $X^{2h}/Z^i$ P value |
|---|---|---|---|---|---|---|---|---|
| | Exp[f] | Con[g] | Diff[h] | | Exp[f] | Con[g] | Diff[h] | |
| Week 0[j] | 235.7 | 237.4 | -1.7 | -0.04[i] 0.96 | 5.6 | 7.5 | -1.9 | -2.25[i] 0.03* |
| Week 5[th,k] | | | | | | | | |
| Week 5[th,L] | 120 | 296.1 | -153.3 | | 4.3 | 7.7 | -3.4 | |
| Week 9[th,M] | 137.3 | 290.6 | -153.3 | | 4.5 | 7.7 | -3.2 | |
| Week 9[th,N] | 128.3 | 268.3 | -140 | | 5.3 | 8.0 | -2.7 | |
| Week 5-0 | 127.3 | 257.2 | -129.9 | | 5.2 | 7.9 | -2.7 | |
| | -115.7 | 58.7 | -142.1 | 13.07 0.001*** | -1.3 | 0.2 | -1 | 1.13 0.28 |
| Week 9-0 | -107.4 | 124.7 | 125.7 | 9.14 0.002** | -0.3 | 0.5 | -0.8 | 0.09 0.75 |
| Week 9-5 | 8.0 | -27.8 | 13.3 | 0.55 0.45 | 1.0 | 0. | 0.7 | 0.001 0.97 |

PS: *P < 0.05.  < 0.01. * P < 0.001.
[a] Sleep efficiency: (total sleep time/time in bed) %.
[b] Sleep time: calculated as SPT (sleep onset and sleep offset) minus deduct WASO (wake after sleep onset).
[c] Awakening time: wake after sleep onset mins and sleep latency.
[d] Number of night time awakenings: wake after sleep onset, frequency of walking.
[e] Exp: Experimental group.
[f] Con: Comparision group.
[g] Diff: Difference between the experimental and comparison groups.
[h] Wald $X^2$: Generalized estimating equation (GEE) interaction (group × time point).
[i] Independent Sample t test: assess the baseline within-group differences.
[j] Week 0: baseline.
[k] Week 5$^{th}$: post 1 (adjusted).
[L] Week 5$^{th}$: post 1 (raw).
[M] Week 9$^{th}$: post 2 (adjusted).
[N] Week 9$^{th}$: post 2 (raw).

Figure 10A:
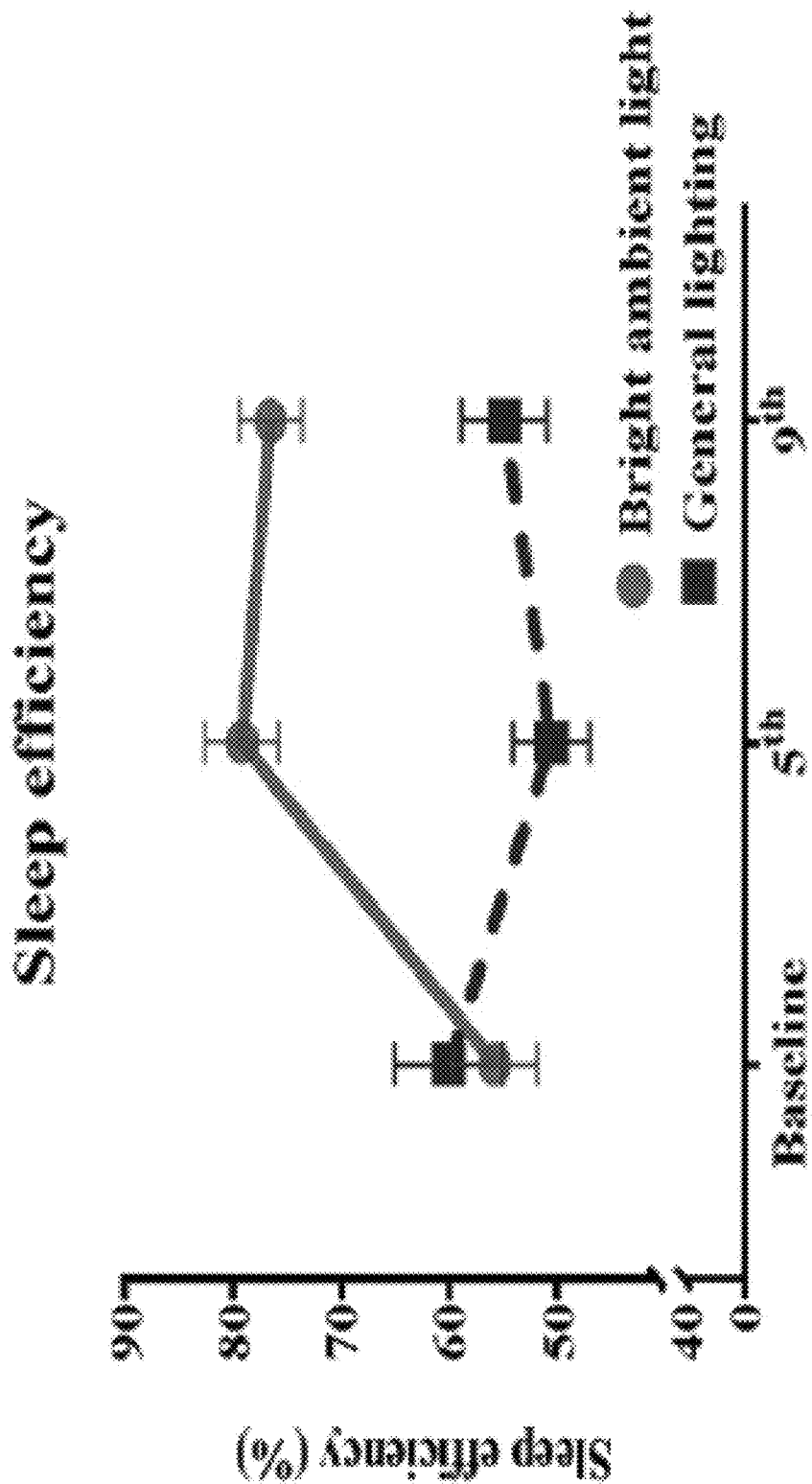
FIG. 10A shows results of the experimental and comparison groups at different time points on sleep efficiency.
Figure 10B:
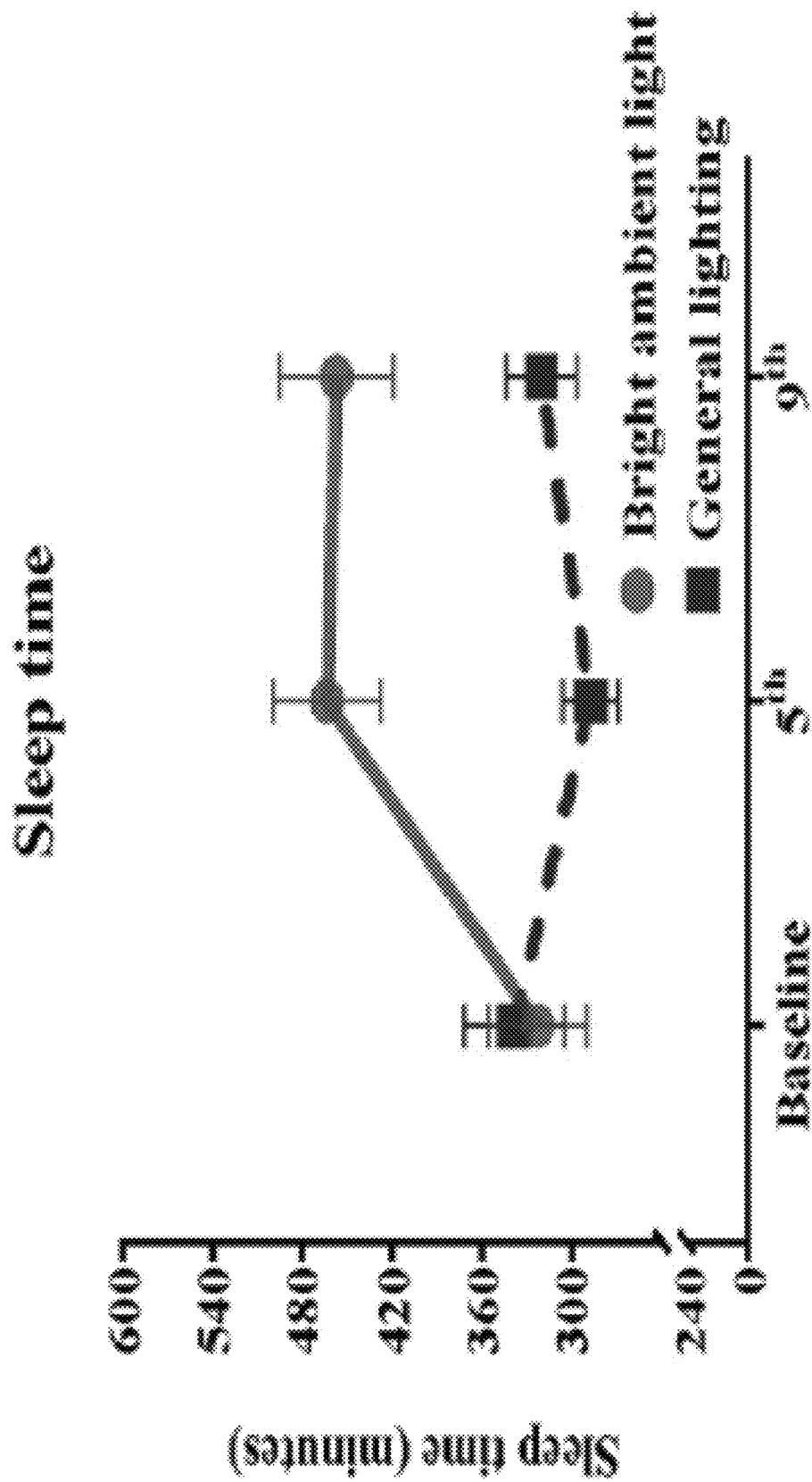
FIG. 10B shows results of the experimental and comparison groups at different time points on sleep time.
Figure 10C:
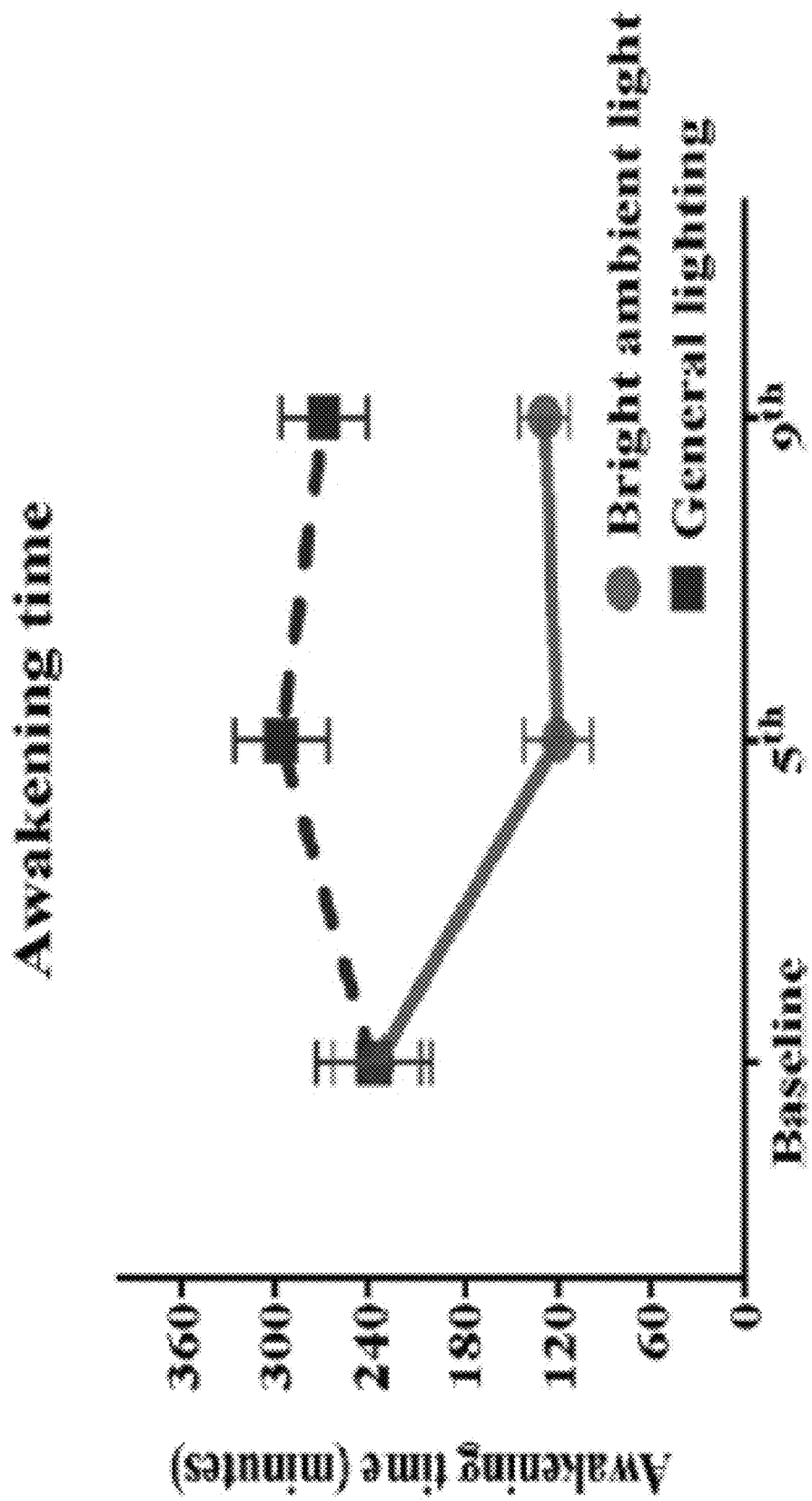
FIG. 10C shows results of the experimental and comparison groups at different time points on awakening time.
Figure 10D:
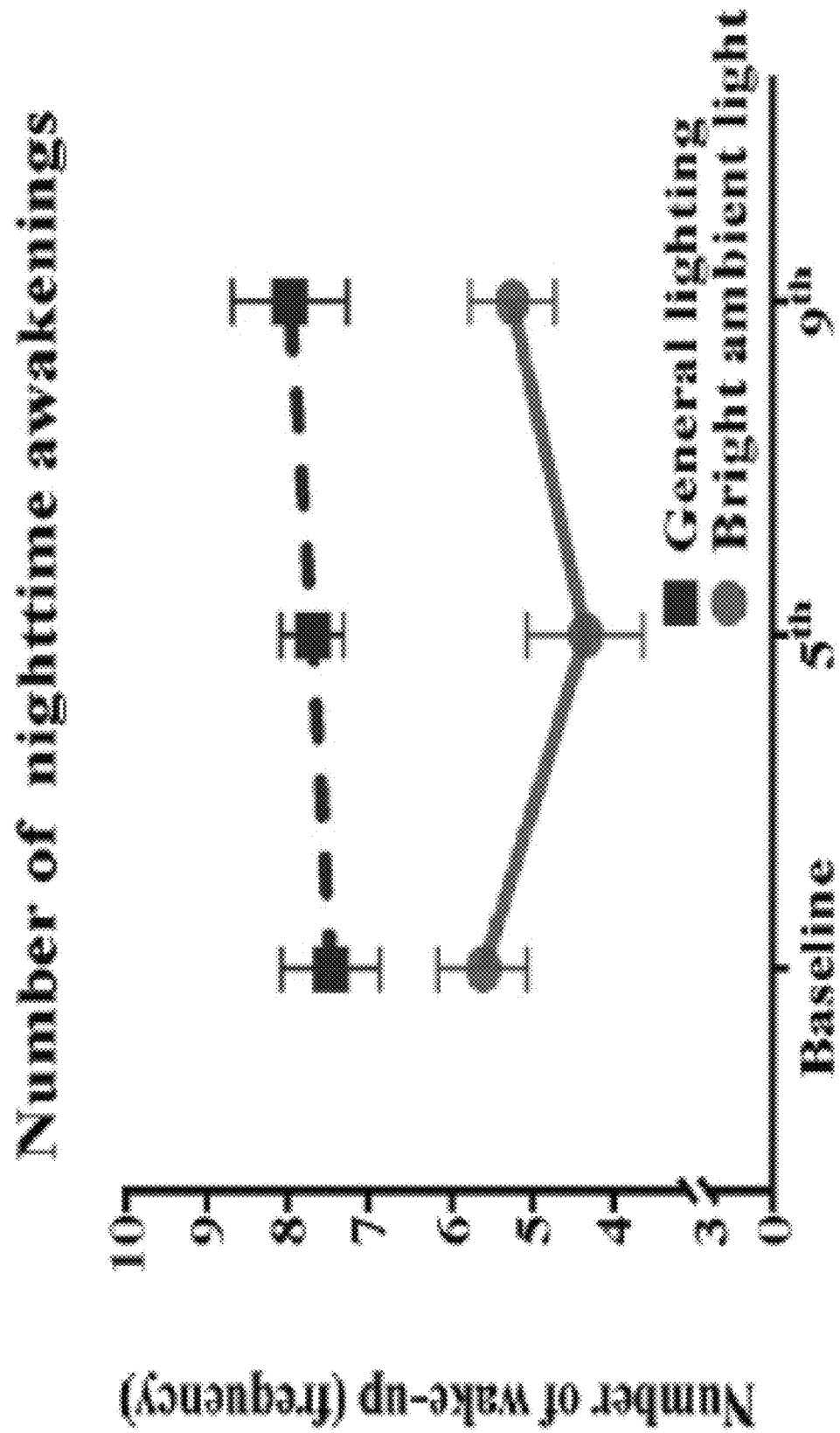
FIG. 10D shows results of the experimental and comparison groups at different time points on number of nighttime awakenings.

Benzodiazepines and total activity in the day were covariates of the main effect of group-by-time interaction on sleep efficiency. FIG. 10A shows the group, time, and interaction effects. The experimental group showed significantly improved sleep efficiency (Wald's test=18.85, P<0.001, and Wald's test=9.91, P=0.002) from baseline to the fifth and ninth week, which was higher than the improvement in the comparison group. Specifically, the experimental group showed a mean increase in sleep efficiency of 41.9% and 37.1% in the fifth and ninth week, respectively (calculation method: (posttest-pretest)/pretest). However, there was no significant difference in the sleep efficiency between the fifth and ninth week (Wald's test=0.9, P=0.33). The experimental group showed a significant improvement in sleep time (Wald's test=11.5, P=0.001, and Wald's test=6.9, P=0.008), which was higher than that in the comparison group (FIG. 10B). Specifically, the experimental group showed a mean increase in sleep time of 141 min (43.7%) and 135 min (41.7%) in the fifth and ninth week, respectively. However, there was no significant difference in sleep time between the fifth and ninth week (Wald's test=0.01, P=0.09). The experimental group showed significant improvement in the awakening time (Wald's test=13.0, P=0.001, and Wald's test=9.1, P=0.002), which was higher than that in the comparison group (FIG. 10C). Specifically, the experimental group showed a mean decrease in awakening time of 116 min (49.1%) and 108 min (45.6%) in the fifth and ninth week, respectively. Moreover, the number of nighttime awakenings decreased by 23.2% (Wald's test=1.1, P=0.28) and 13.5% (Wald's test=0.09, P=0.75) in the experimental and comparison groups, respectively, with no difference between the fifth and ninth week (FIG. 10D). The experimental group's improvement was most pronounced for awakening time, followed by sleep time, sleep efficiency, and number of nighttime awakenings. As shown in Table 1, the comparison group showed more severe sleep disturbances in sleep efficiency, sleep time, awakening time, and the number of nighttime awakenings at the fifth and ninth week than at baseline.

3.3. Effect of Bright Ambient Light on Circadian Rhythms

Figure 11A:
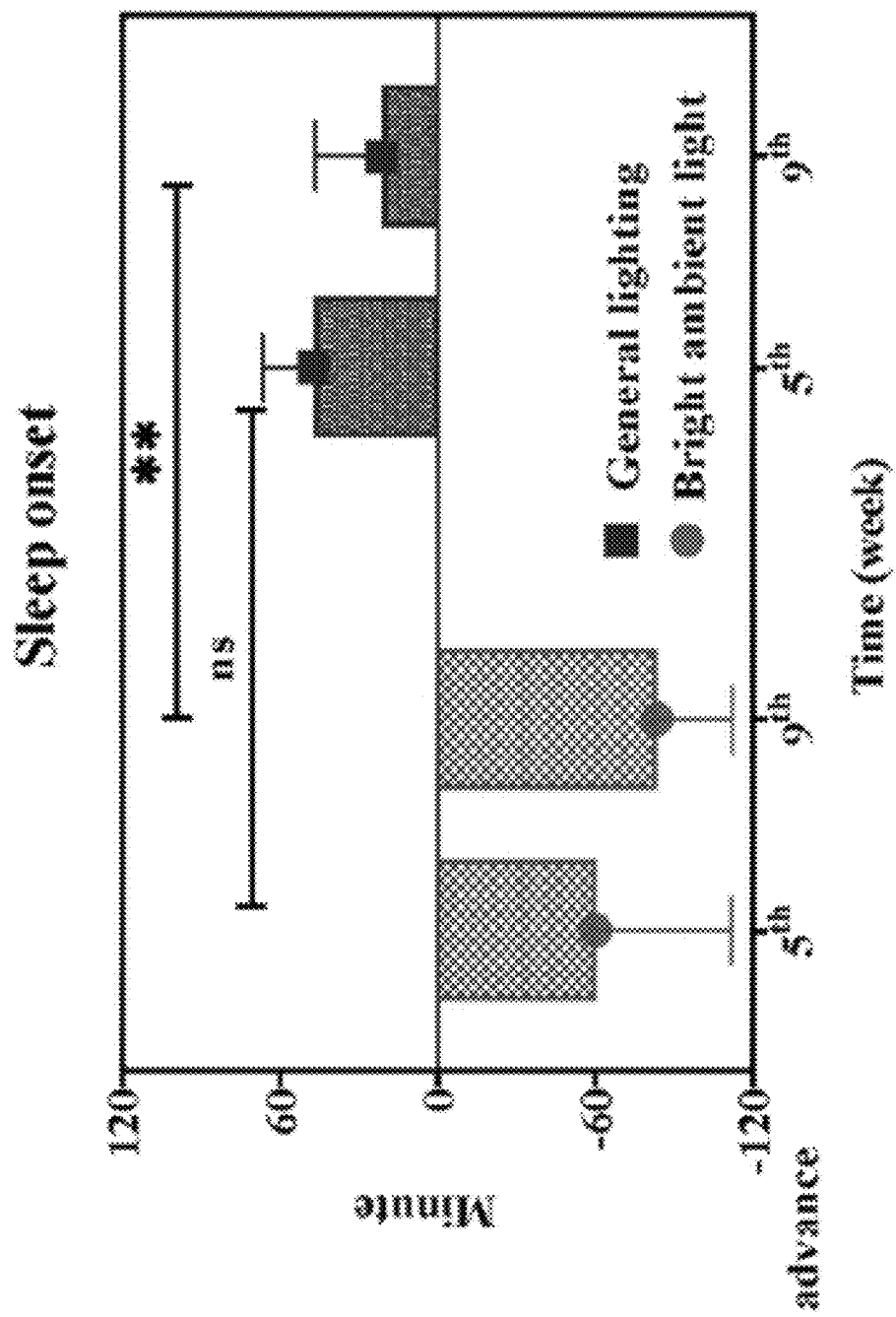
FIG. 11A shows results of the experimental and comparison groups at different time points on sleep onset.
Figure 11B:
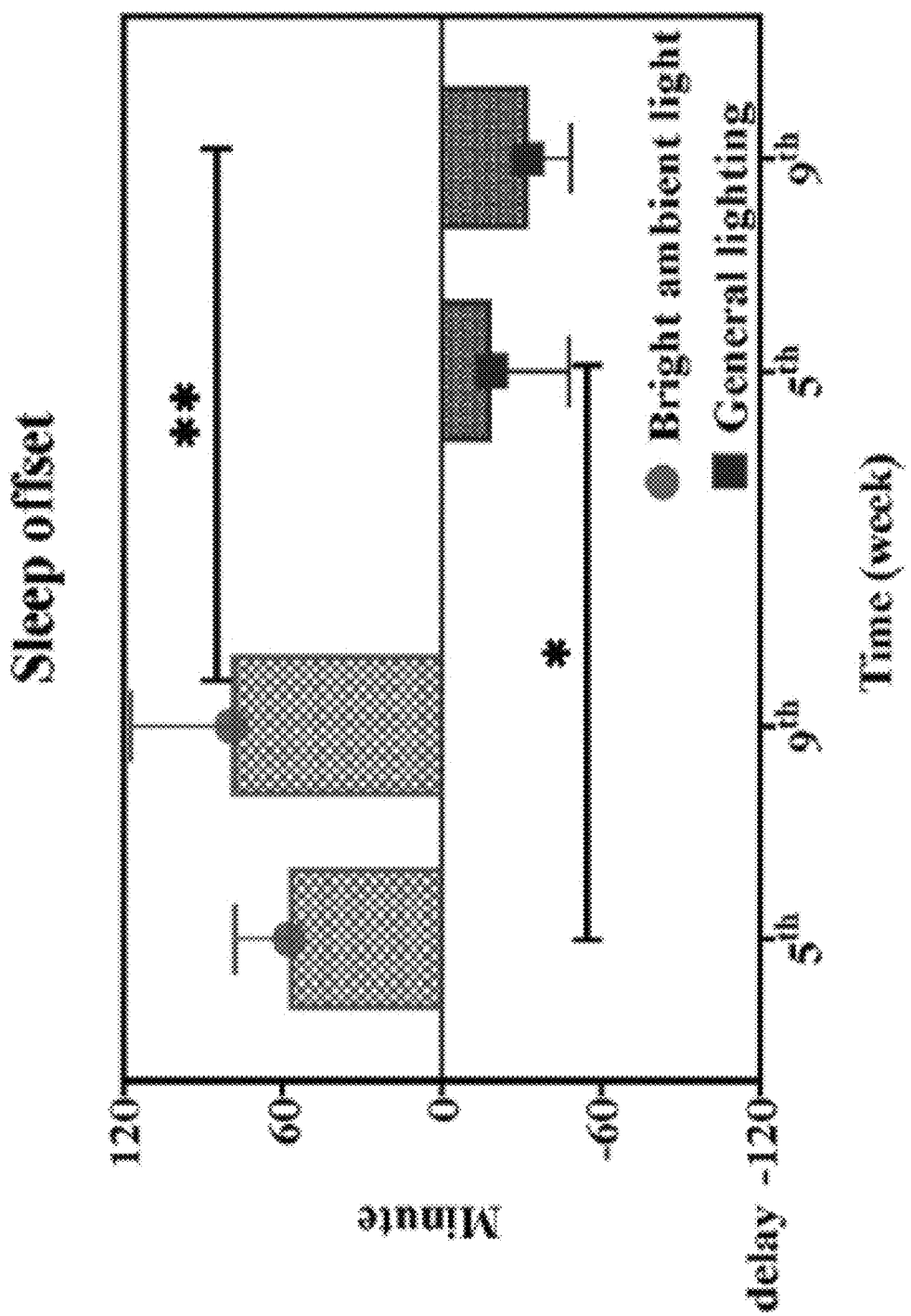
FIG. 11B shows results of the experimental and comparison groups at different time points on sleep offset.

The experimental group showed significant improvement in sleep onset (Wald's test=2.42, P>0.05, and Wald's test=5.03, P<0.01), which was higher than that in the comparison group. Specifically, sleep onset in the experimental group was advanced by 60 min and 84 min in the fifth and ninth week, respectively. Contrastingly, the comparison group showed delayed sleep onset at the fifth (47 min) and ninth week (21 min) than at baseline. The experimental group showed a significant improvement in sleep offset (Wald's test=4.72, P<0.05, and Wald's test=7.41, P<0.01), which was higher than that in the comparison group. Specifically, the sleep offset in the experimental groupced delayed by 57 min and 79 min in the fifth and ninth week, respectively. Contrastingly, the comparison group showed earlier sleep offset at fifth (by 19 min) and ninth (by 32 min) week than at baseline, as shown in FIG. 11 and Table 2.

TABLE 2

Changes in the circadian rhythms of two groups at different time points.

| | Bright ambient light | | | | General fighting | | | |
|---|---|---|---|---|---|---|---|---|
| | Sleep onset | | Sleep offset | | Sleep onset | | Sleep offset | |
| | Mean | SE | Mean | SE | Mean | SE | Mean | SE |
| Baseline | 23:36 | ±42.14 | 05:50 | ±25.13 | 22:11 | ±28.71 | 07:14 | ±11.43 |
| $5^{th}$ week | 22:36 | ±51.88 | 06:47 | ±20.62 | 22:58 | ±19.69 | 06:55 | ±29.29 |
| $9^{th}$ week | 22:13 | ±28.79 | 07:09 | ±37.5 | 22:32 | ±25.42 | 06:41 | ±16.33 |

This example shows that ambient bright light is more effective than general lighting in the amelioration of sleep disturbances and improvement of circadian rhythms in older adults with dementia. Specifically, ambient bright light therapy significantly increases sleep efficiency and sleep time, as well as decreased awakening time. In the fifth and ninth week, respectively, sleep onset can be advanced by 60 min and 84 min, while sleep offset can be delayed by 57 min and 79 min relative to baseline.

4. Dementia Symptoms and Cognitive Function 4.1 Participants' Demographic and Clinical Characteristics Thirty-five participants completed the baseline assessment, and 29 and 22 participants completed the 5th and 9th week assessments, respectively. No statistically significant differences were observed in the demographic characteristics (educational level, marital status, sleep pattern, dementia type, dementia severity, and source at baseline or in the 5th and 9th weeks) between the experimental and comparison groups. This finding indicated a homogeneous distribution of participants. Conversely, a statistically significant difference was observed in sex, with male participants comprising 5.9 and 33% of the experimental group and comparison group, respectively (P<0.05); most of the participants were female. The Mann-Whitney U test was used to assess the baseline age, NPI and MMSE scores, and medication, and the results showed no significant differences in age, medication, and MMSE scores. However, a statistically significant difference (NPI mean of 36 fractions for the experimental group and 21 fractions for the comparison group; P<0.006) was observed in the NPI scores between the two groups. The experimental group had more serious BPSD than the comparison group at baseline.

Figure 12:
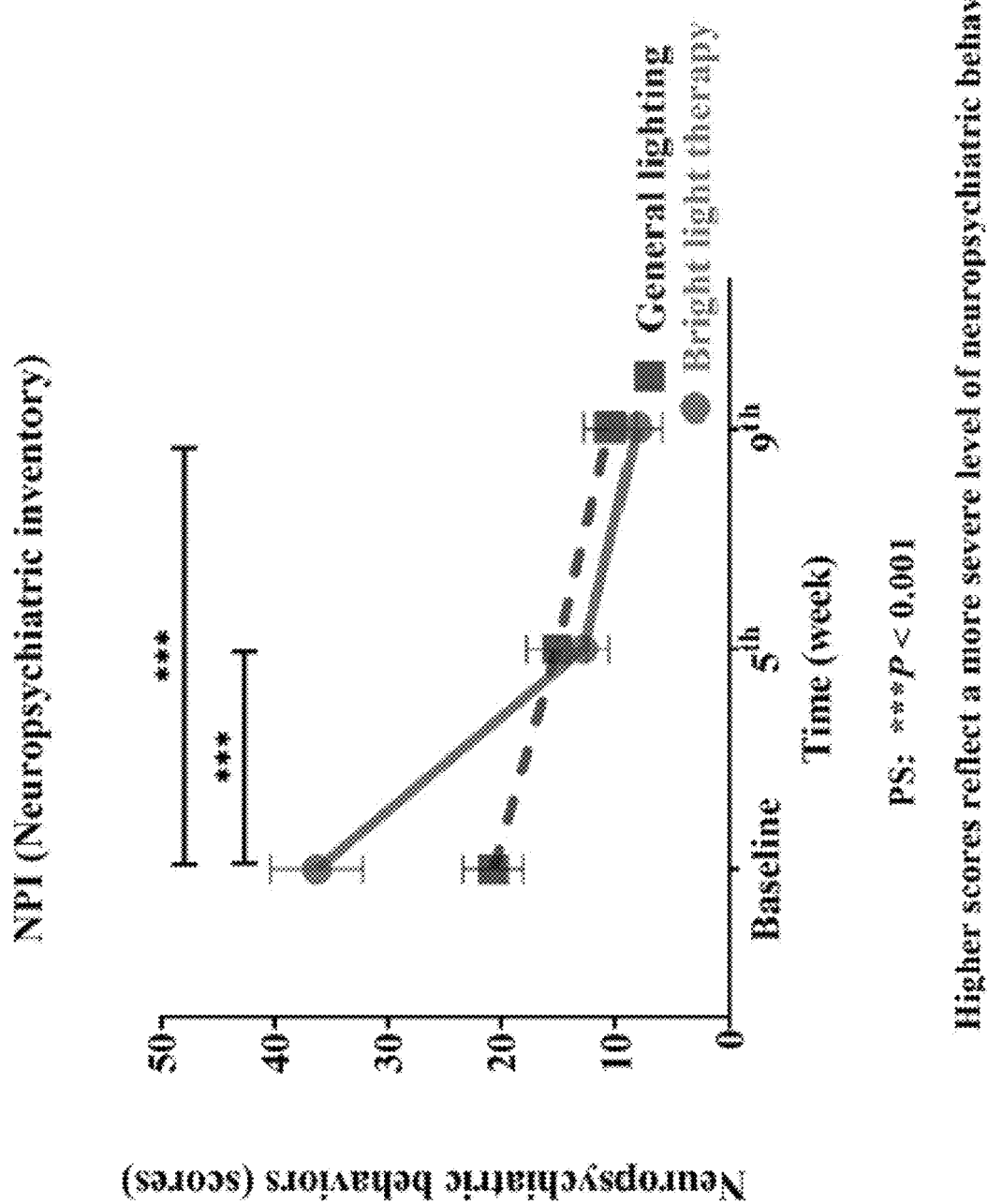
FIG. 12 shows that the experimental group showed significant improvement in the NPI (Wald's test=12.59, P<0.001; Wald's test=10.39, P=0.001) from baseline to the 5th and 9th weeks compared with the comparison group.

4.2 Primary Outcomes 4.2.1 Effect of Bright Light Therapy on Behavioral and Psychological Symptoms of Dementia The NPI was used as the neuropsychiatric behavior outcome indicator of the effects of bright light intervention. The experimental group showed a significant improvement in the NPI (Wald's test=12.59, P<0.001; Wald's test=10.39, P=0.001) from baseline to the $5^{th}$ and $9^{th}$ weeks compared with the comparison group. The main effect on BPSD was evidenced by a significant change in the slope, reflecting improvements in BPSD (FIG. 12). The experimental group showed a significant improvement in the NPI, with a mean decrease of 65% (calculation method: pretest-posttest/pretest) and 78% in the $5^{th}$ and $9^{th}$ weeks, respectively. However, the differences in the NPI at the 5th and 9th weeks were not significant (Wald's test=0.2, P=0.65).

4.2.2 Effect of Bright Light Therapy on Cognitive Function

Figure 13:
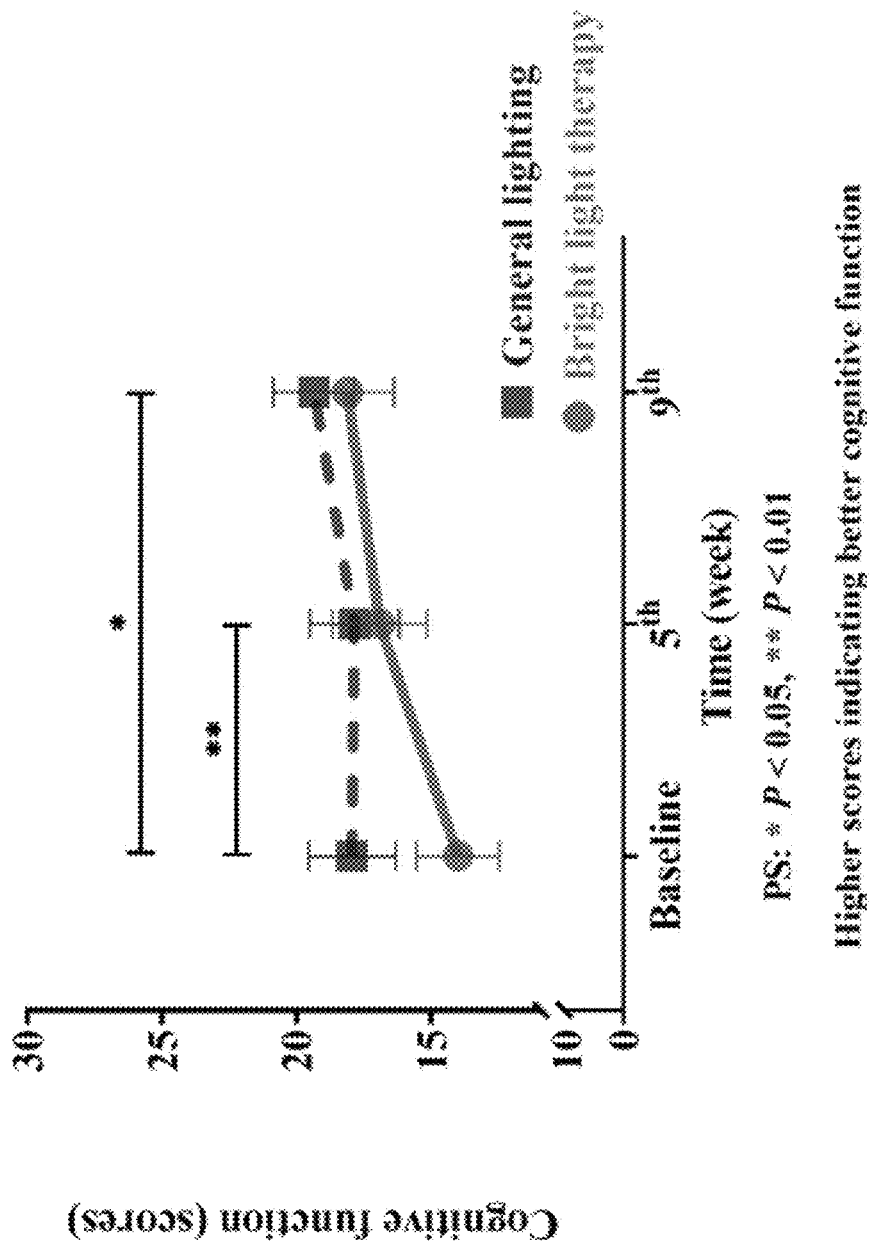
FIG. 13 shows that the experimental group showed a significant improvement in the MMSE score (Wald's test=7.2, P<0.007; Wald's test=3.9, P=0.04) from baseline to the 5th and 9th weeks compared with the comparison group.

The MMSE was used as the cognitive function outcome indicator of the effects of the group bright light therapy intervention. The experimental group showed significant improvement in the MMSE score (Wald's test=7.2, P<0.007; Wald's test=3.9, P=0.04) from baseline to the 5th and 9th weeks compared with the comparison group. A main effect on cognitive function was observed. A significant change in the slope reflects improved cognitive function (FIG. 13). The experimental group showed a significant improvement in the MMSE score, with mean increases of 19% (calculation method: posttest-pretest/pretest) and 28% in the 5th and 9th weeks, respectively. However, the MMSE scores in the 5th and 9th weeks were not significantly different (Wald's test=1.5; P=0.20).

4.3 Secondary Outcomes

Figure 14A:
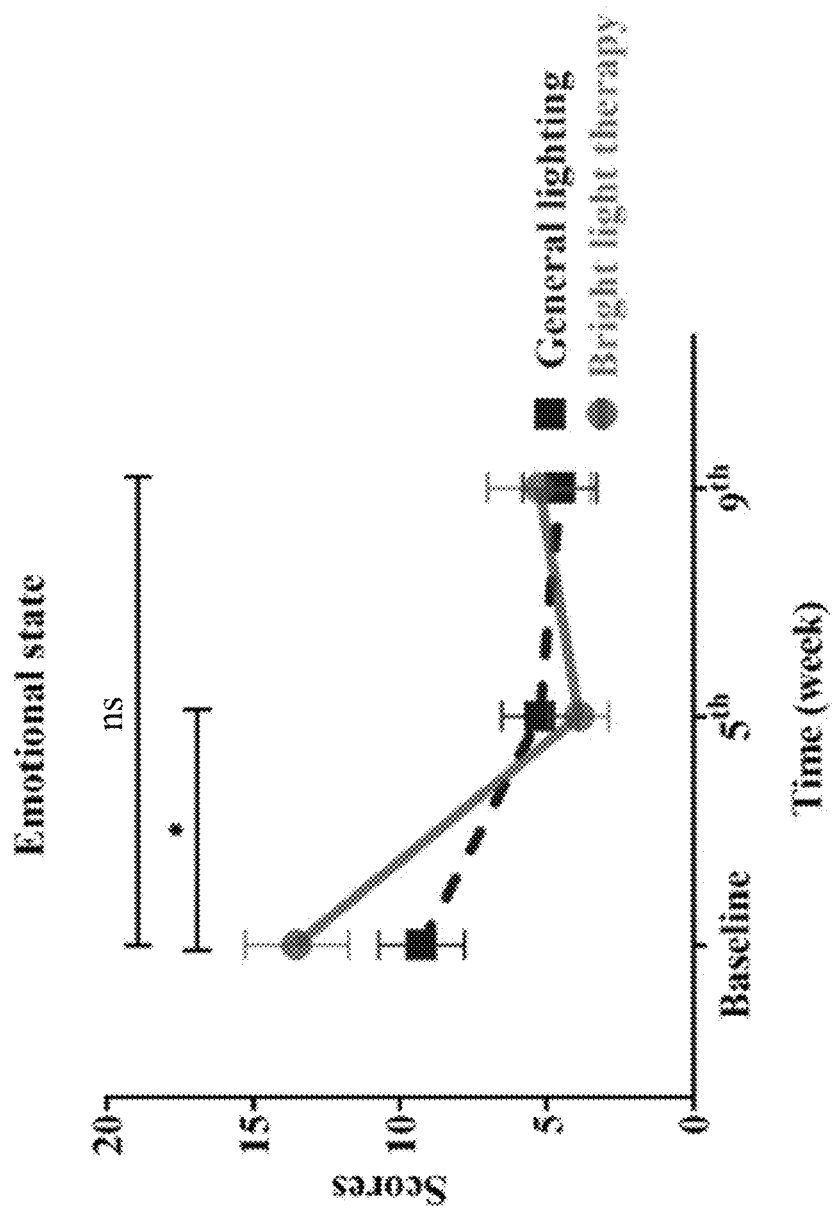
FIG. 14A shows results of the experimental and comparison groups at different time points on emotional state.
Figure 14B:
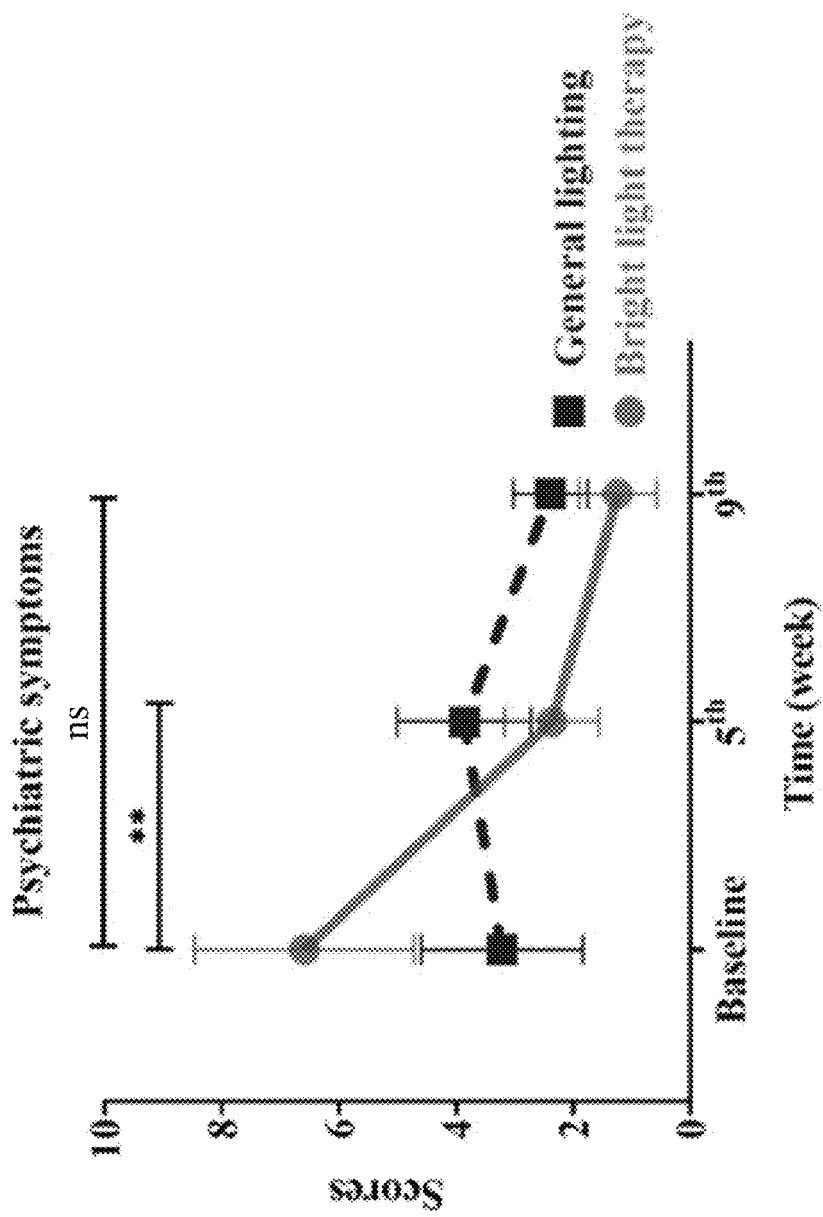
FIG. 14B shows results of the experimental and comparison groups at different time points on psychiatric symptoms.
Figure 14C:
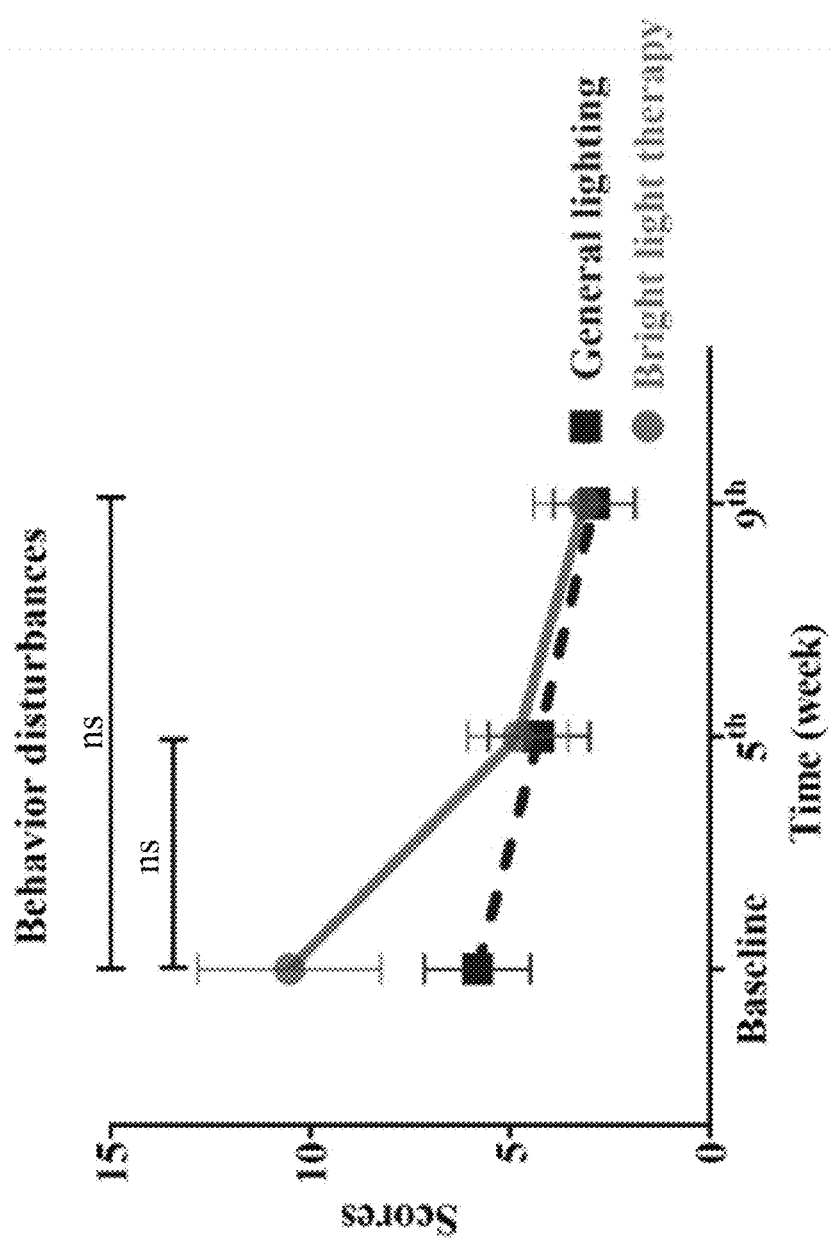
FIG. 14C shows results of the experimental and comparison groups at different time points on behavioral disturbances.
Figure 14D:
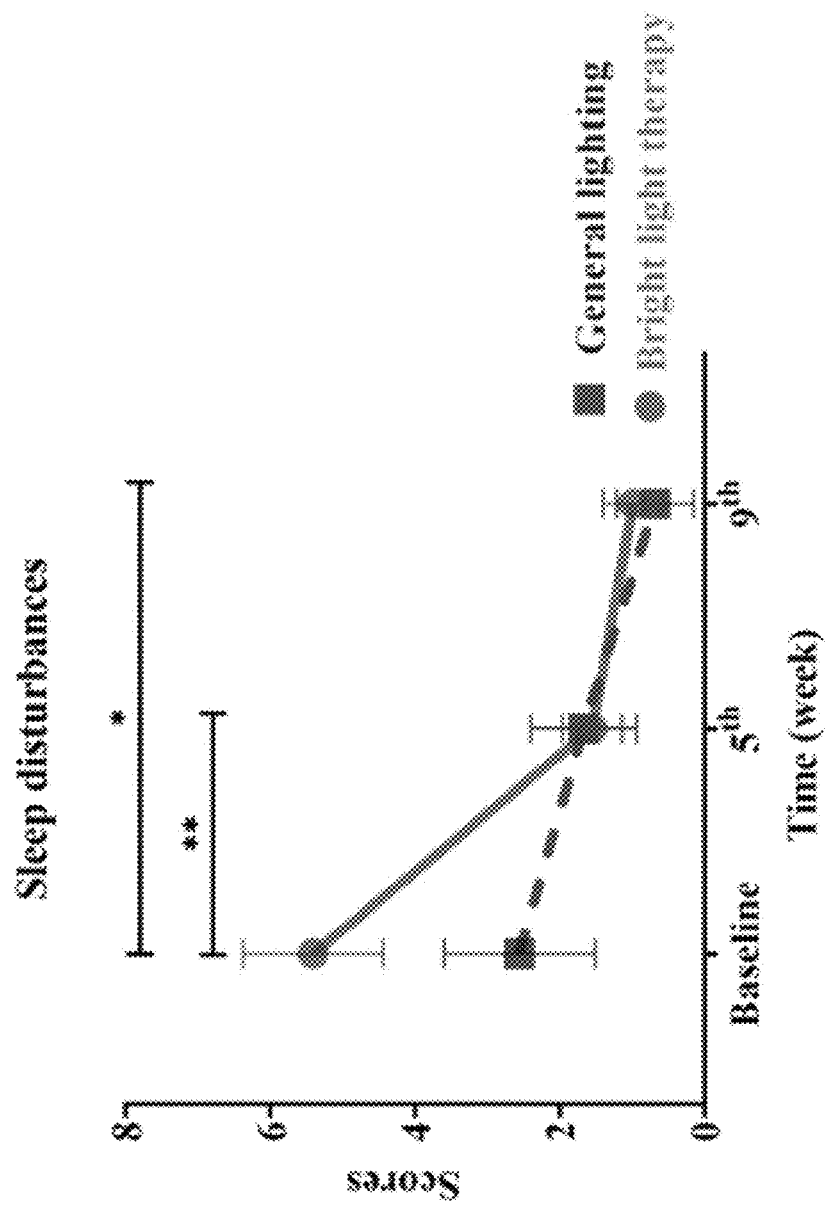
FIG. 14D shows results of the experimental and comparison groups at different time points on sleep disturbances.

The NPI is categorized into assessments of the emotional state, psychiatric symptoms, behavioral disturbances, and sleep disturbances (FIG. 14A-D). Regarding the specific neuropsychiatric behavioral domains of the emotional state, psychiatric symptoms, and sleep disturbances, continuous, promising improvements were observed in sleep disturbances (FIG. 14D). The experimental group showed significant improvement in sleep disturbances (Wald's test=3.9, P<0.002; Wald's test=10.0, P=0.04) from baseline to the 5th and $9^{th}$ weeks, which was greater than that in the comparison group.

The experimental group showed a greater mean improvement than the baseline; the highest value was observed for sleep disturbances, followed by psychiatric symptoms, emotional state, and behavioral disturbances. However, the greatest mean improvement in the comparison group was observed for sleep disturbances, followed by emotional state, behavioral disturbances, and psychiatric symptoms. For both the experimental and comparison groups, the domain with the maximum change was psychiatric symptoms (FIG. 14B).

Figure 15A:
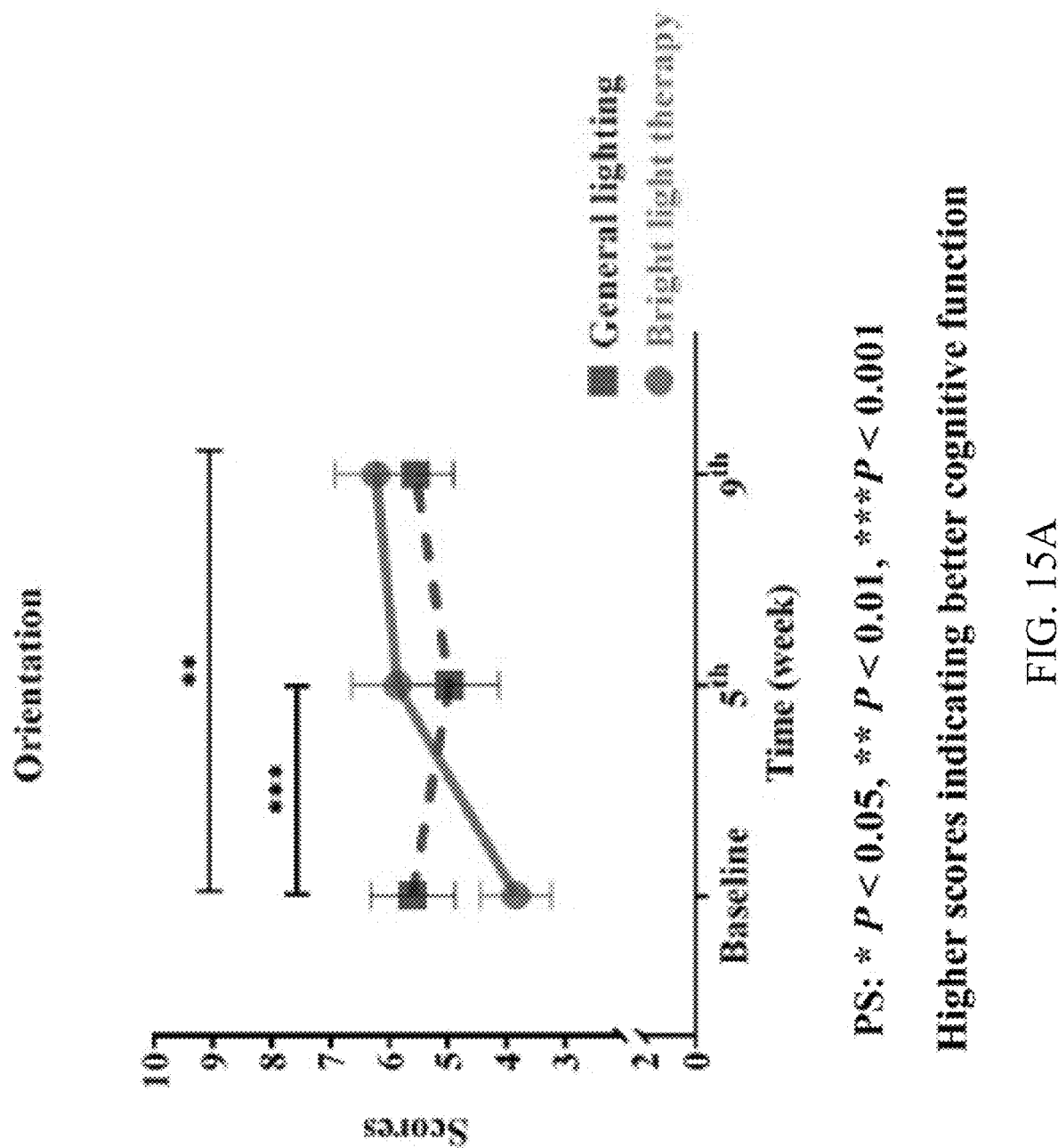
FIG. 15A shows results of the experimental and comparison groups at different time points on orientation.
Figure 15B:
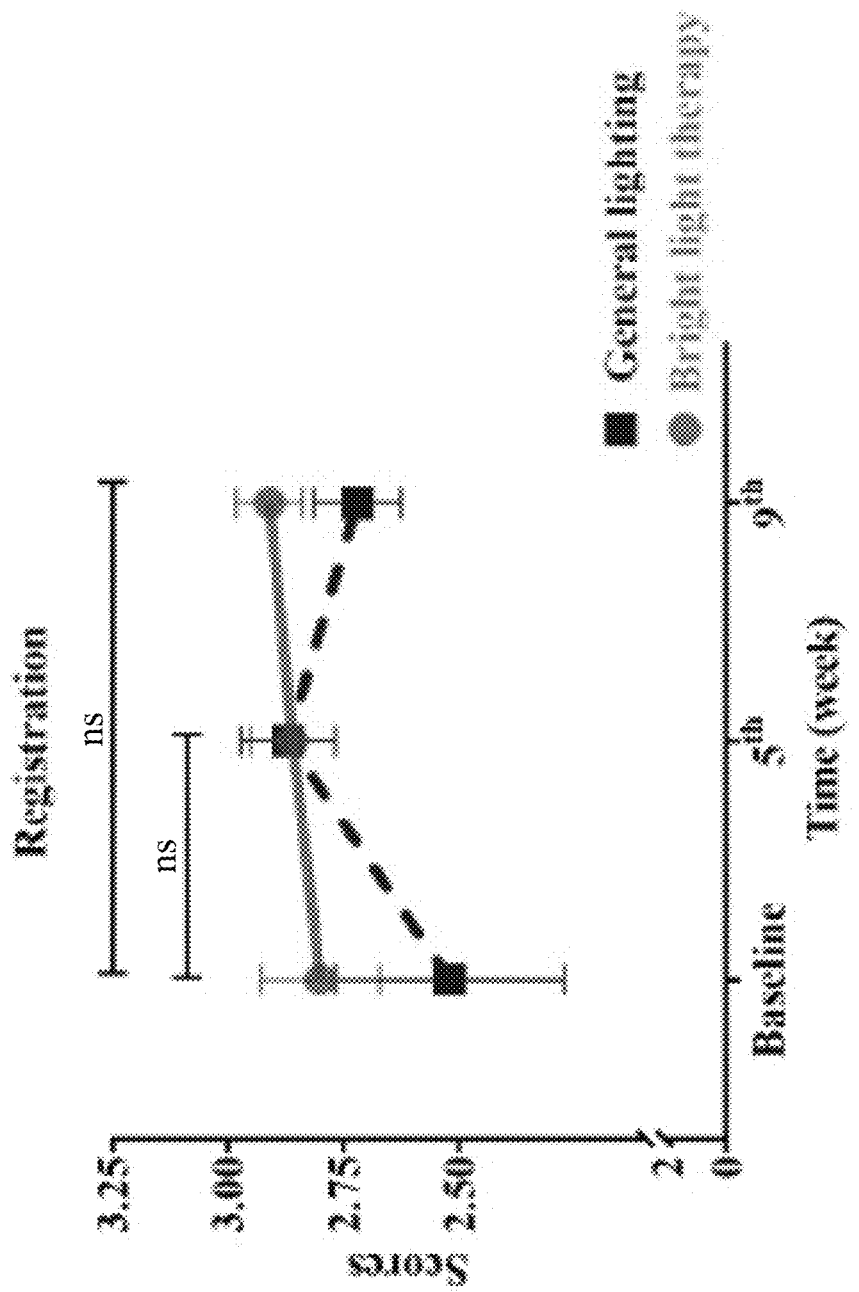
FIG. 15B shows results of the experimental and comparison groups at different time points on registration.
Figure 15C:
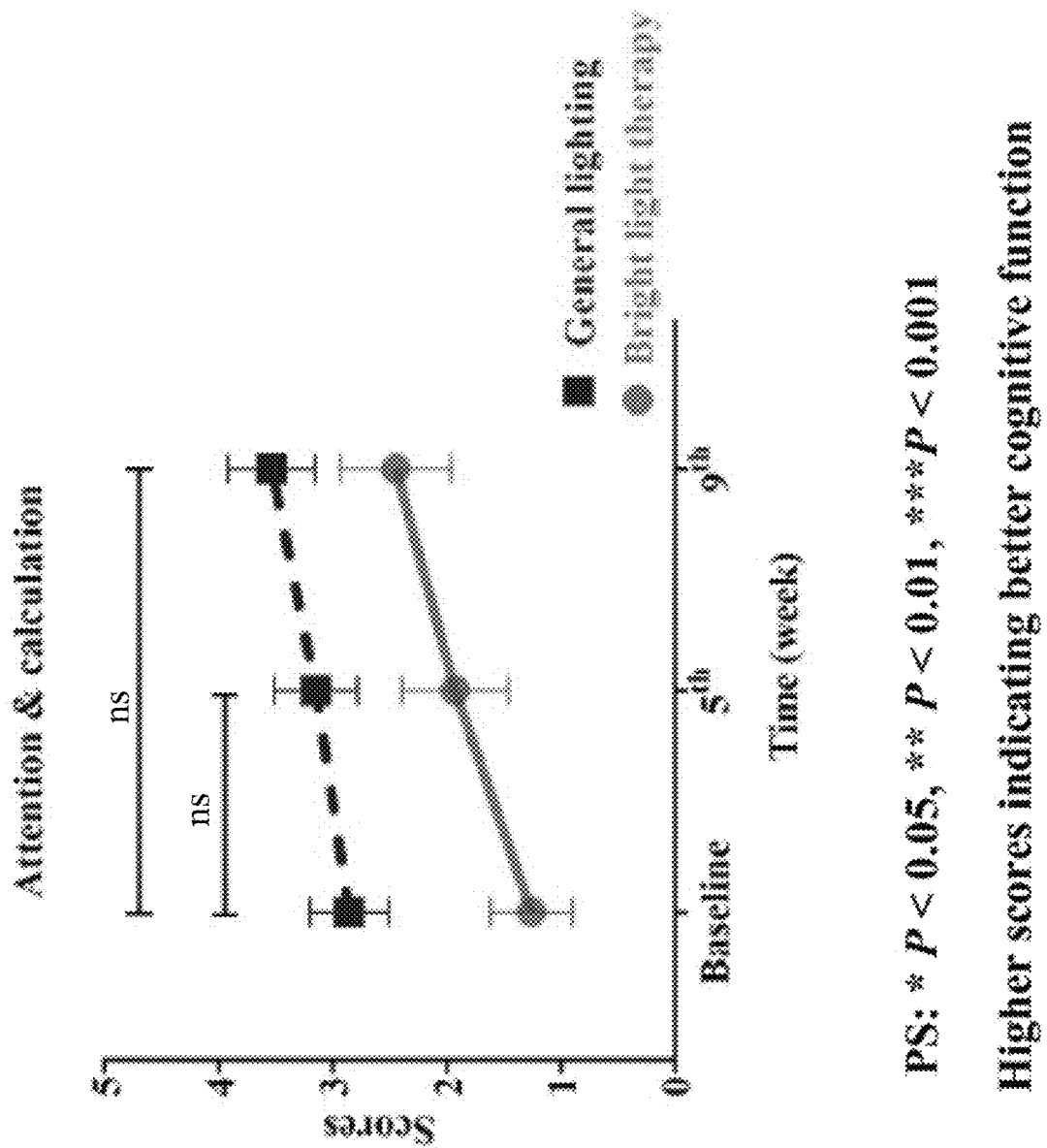
FIG. 15C shows results of the experimental and comparison groups at different time points on attention and calculation.
Figure 15D:
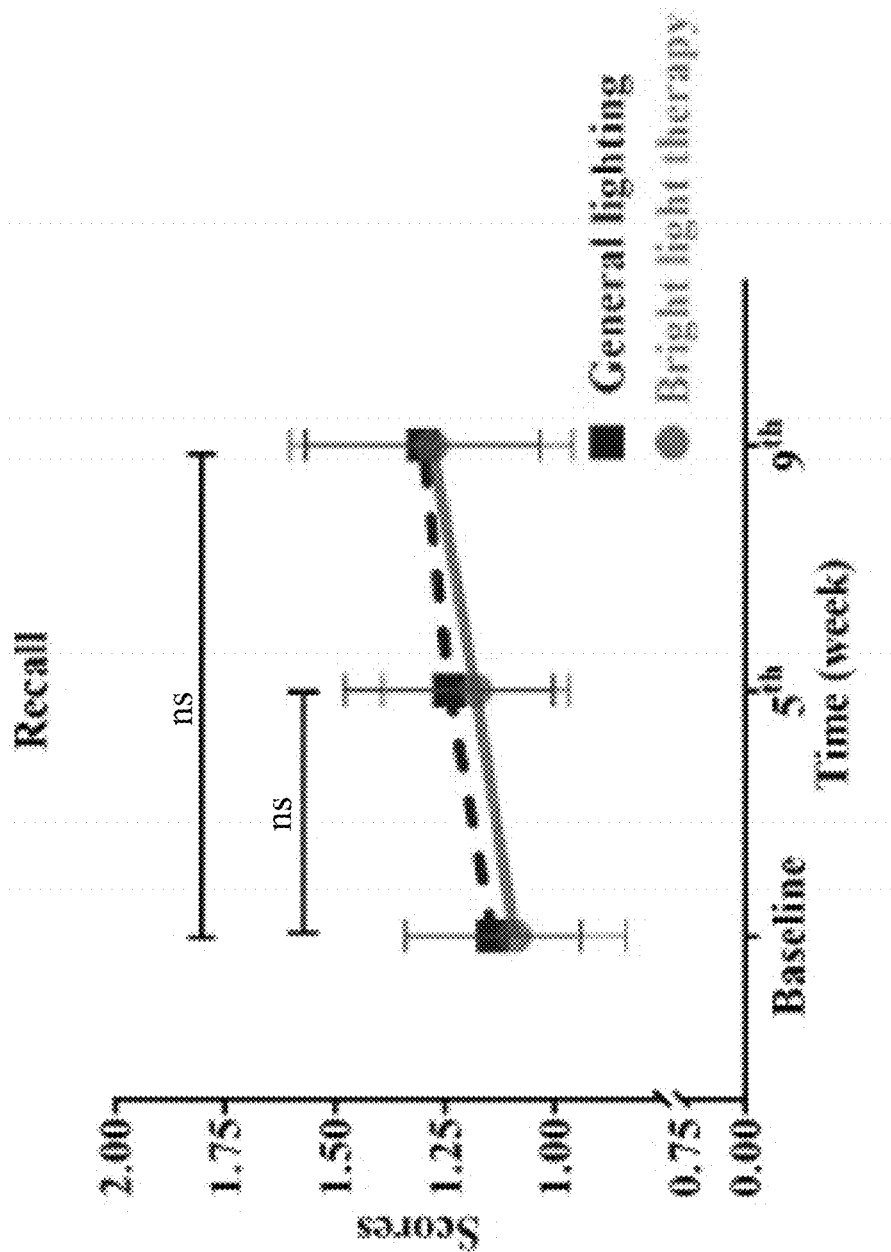
FIG. 15D shows results of the experimental and comparison groups at different time points on recall.
Figure 15E:
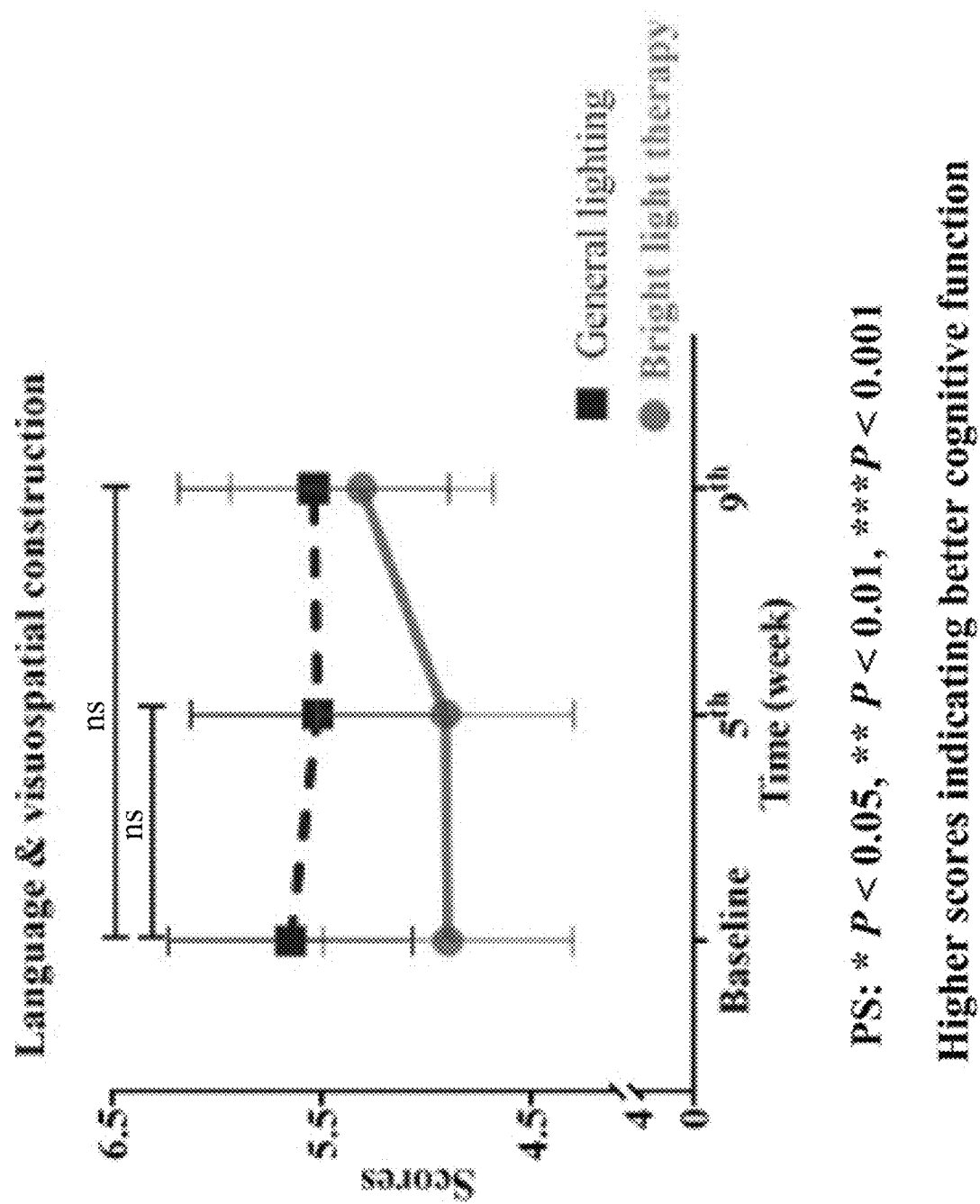
FIG. 15E shows results of the experimental and comparison groups at different time points on language and visuospatial construction.

The MMSE is categorized into orientation, registration, attention and calculation, recall, and language visuospatial construction (FIG. 15A-E). Regarding the specific cognitive function domains, a significant change in the slope reflected a better status in terms of orientation, registration, attention calculation, recall, and language visuospatial construction. Among these domains, orientation showed the greatest improvement (FIG. 15A). The experimental group showed a significant improvement in orientation (Wald's test=10.1, P=0.001; Wald's test=8.73, P=0.003) from baseline to the 5th and 9th weeks, which was greater than that of the comparison group.

The experimental group showed greater improvements in attention and calculation, followed by orientation, recall, language visuospatial construction, and registration compared with the baseline value. However, the greatest improvements in the comparison group were observed for attention and calculation, followed by recall, registration, language visuospatial construction, and orientation. For both the experimental and comparison groups, the domain with the maximum change was orientation (FIG. 15A).

This example showed that bright light therapy was more effective than general lighting at improving BPSD and cognitive function among older adults with dementia. Bright light therapy reduced BPSD and enhanced cognitive function. Although the outcomes at the 5th and 9th weeks were not significantly different, 4 weeks of bright light therapy achieved a significant effect. Therefore, 4 weeks of therapy is recommended because it also requires a comparatively shorter duration of high adherence and acceptability from the participants. Regarding the NPI subdomains, a significant improvement in sleep disturbances was observed. The NPI subdomain with the greatest mean improvement was sleep disturbances for both the experimental and comparison groups; the domain with the maximum change for both groups was psychiatric symptoms. Regarding specific cognitive domains, the domains with the greatest mean improvement were attention and calculation for both the experimental and comparison groups; the domain with the maximum change in the two groups was orientation.

As used herein, the singular terms "a," "an," and "the" may include a plurality of referents unless the context clearly dictates otherwise.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same or equal if the difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" parallel can refer to a range of angular variation relative to 0° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°. For example, "substantially" perpendicular can refer to a range of angular variation relative to 90° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range were explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein are described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations on the present disclosure.

What is claimed is:

1. A light system used in an ambient environment, comprising:
   an emitting device configured to provide a light impinging on a subject in the ambient environment, wherein the emitting device is positioned relative to the subject so that a line extending from the emitting device to the subject and a horizontal plane at a same level as an eye of the subject form an angle of 45 degrees; and
   a controller electrically coupled to the emitting device and configured to control the emitting device;
   wherein the light provided by the emitting device has at least 30% green light, and the light has a horizontal illuminance of 2200 lux to 2800 lux and a vertical illuminance of 3600 lux to 4800 lux.

2. The light system of claim 1, wherein the horizontal illuminance of the light is measured on a vertical plane at the eye of the subject.

3. The light system of claim 1, wherein a color temperature of the light provided by the emitting device is at least 4,000 K.

4. The light system of claim 1, wherein the green light has a blue-green light spectral component with a wavelength from 450 nm-580 nm.

5. A light system in an ambient environment, comprising:
   an emitting device configured to provide a light into the ambient environment, wherein the emitting device is positioned relative to the subject so that a line extending from the emitting device to the subject and a horizontal plane at a same level as an eye of the subject form an angle of 45 degrees, wherein the light has at least 30% green light; and a controller electrically connected to the emitting device, wherein the controller comprises:
- a control module configured to control the emitting device;
- a sensing module configured to detect a horizontal illuminance and a vertical illuminance of the light provided by the emitting device, wherein the controller is configured to control the emitting device so that the horizontal illuminance is from 2200 lux to 2800 lux and the vertical illuminance is from 3600 lux to 4800 lux; and
- a control interface in communication with the control module.

6. The light system of claim 5, wherein the controller module is in communication with the sensing module and controls the emitting device based on the horizontal illuminance and the vertical illuminance detected by the sensor.

7. The light system of claim 5, wherein the vertical illuminance is measured from an amount of the light on the horizontal plane at the eye of the subject in the ambient environment.

8. The light system of claim 5, wherein the horizontal illuminance is measured from an amount of the light on a vertical plane at the eye of the subject in the ambient environment.

9. The light system of claim 5, wherein the emitting device comprises at least two block lamps, and wherein the at least two block lamps are configured to be tiled with each other.

10. The light system of claim 5, wherein the emitting device comprises a diffusing fitting.

11. The light system of claim 5, further comprising an adjusting mechanism electrically connected to the emitting device and configured to move the emitting device.

12. A method for providing ambient lighting for improving one or more of sleeping quality, circadian rhythms, cognitive function, neurological disorder, depression, emotional status, heart rate variability, sympathetic activity and parasympathetic activity in a subject, comprising:
providing light into an ambient environment, wherein a ratio of a blue-green light with a wavelength from 450 nm to 580 nm is increased to at least 30%;
adjusting the light so that a horizontal illuminance of the light is 2200 lux to 2800 lux and a vertical illuminance of the light is 3600 lux to 4800 lux; and
exposing the subject to the light, such that an optical axis of the light and a horizontal plane at a same level as an eye of the subject form an angle of 45 degrees.

13. The method of claim 12, wherein the horizontal illuminance of the light is measured from an amount of the light on a vertical plane at the eye of the subject.

14. The method of claim 12, further comprising: adjusting the optical axis of the light so that the optical axis of the light and the horizontal plane at an eye of the subject form the angle of 45 degrees.

15. The method of claim 12, wherein a ratio of a blue light spectral component with a wavelength from 415 nm-460 nm is decreased.

16. The method of claim 15, wherein a ratio of a blue light spectral component with a wavelength from 465 nm-490 nm is maintained.

17. The method of claim 12, wherein the vertical illuminance of the light is measured from an amount of the light on a horizontal plane at the eye of the subject.

18. The method of claim 12, wherein the light has a color temperature at least 4,000 K.

* * * * *